(12) United States Patent
Kaplan et al.

(10) Patent No.: US 9,347,951 B2
(45) Date of Patent: May 24, 2016

(54) FUSION PROTEIN COMPRISING THE EXTRACELLULAR DOMAIN OF A FILOVIRUS GLYCOPROTEIN FUSED TO AN IMMUNOGLOBULIN HEAVY CHAIN CONSTANT REGION

(75) Inventors: Gerardo Kaplan, Rockville, MD (US); Krishnamurthy Konduru, Rockville, MD (US); Jerome Jacques, Bethesda, MD (US); Sina Bavari, Frederick, MD (US); Steven Bradfute, Albuquerque, NM (US)

(73) Assignee: THE UNITED STATES OF AMERICA AS REPRESENTED BY THE SECRETARY OF THE DEPARTMENT OF HEALTH AND HUMAN SERVICES, NATIONAL INSTITUTES OF HEALTH, Washington, DC (US)

( * ) Notice: Subject to any disclaimer, the term of this patent is extended or adjusted under 35 U.S.C. 154(b) by 98 days.

(21) Appl. No.: 13/882,041

(22) PCT Filed: Oct. 28, 2011

(86) PCT No.: PCT/US2011/058418
§ 371 (c)(1),
(2), (4) Date: Aug. 16, 2013

(87) PCT Pub. No.: WO2012/154203
PCT Pub. Date: Nov. 15, 2012

(65) Prior Publication Data
US 2013/0323243 A1    Dec. 5, 2013

Related U.S. Application Data

(60) Provisional application No. 61/407,842, filed on Oct. 28, 2010.

(51) Int. Cl.
*G01N 33/68* (2006.01)
*A61K 39/12* (2006.01)
*G01N 33/569* (2006.01)
*C07K 14/005* (2006.01)
*A61K 39/00* (2006.01)

(52) U.S. Cl.
CPC ............ *G01N 33/6854* (2013.01); *A61K 39/12* (2013.01); *C07K 14/005* (2013.01); *G01N 33/56983* (2013.01); *A61K 2039/55561* (2013.01); *A61K 2039/55566* (2013.01); *A61K 2039/55577* (2013.01); *A61K 2039/6056* (2013.01); *C07K 2319/30* (2013.01); *C07K 2319/43* (2013.01); *C12N 2760/14122* (2013.01); *C12N 2760/14134* (2013.01); *G01N 2333/08* (2013.01); *G01N 2469/20* (2013.01); *G01N 2800/26* (2013.01)

(58) Field of Classification Search
CPC .............. G01N 33/6854; A61K 39/12; C12N 2760/14122; C12N 2760/14134; C07K 2319/30
See application file for complete search history.

(56) References Cited

U.S. PATENT DOCUMENTS 7,754,855 B1 *   7/2010   Cox et al. ...................... 530/350
2003/0224015 A1   12/2003   Hart et al.

FOREIGN PATENT DOCUMENTS

WO   WO 01/07081 A1   2/2001
WO   WO 2006/046963 A2   5/2006

OTHER PUBLICATIONS

Sanchez, A., et al., Apr. 1996, The virion glycorproteins of Ebola viruses are encoded in two reading frames and are expressed through transcriptional editing, Proc. Natl. Acad. Sci. USA 93:3602-3607.*
Reed, D. S., and M. Mohamadzadeh, 2007, Status and challenges of filovirus vaccines, Vaccine 25:1923-1934.*
Phoolcharoen Waranyoo, et al., "Transient Expression of Ebola Immune Complex in Nicotiana benthamiana," *Plant Physiology*, Plant Biology (Rockville) 2009—Joint Annual Meeting of the American-Society-of-Plant-Biologists/American Society of Plant Physiologists, vol. 2009, Suppl. S (Jan. 1, 2009).
Phoolcharoen Waranyoo, et al., "Expression of an immunogenic Ebola immune complex in Nicotiana benthamiana," *Plant Biotechnology Journal*, vol. 9(7), pp. 807-816 (Sep. 1, 2011).
Konduru, K., et al., "Ebola virus glycoprotein Fc fusion protein confers protection against lethal challenge in vaccinated mice," *Vaccine*, vol. 29(16), pp. 2968-2977 (Apr. 2011).

* cited by examiner

*Primary Examiner* — Jeffrey Parkin
(74) *Attorney, Agent, or Firm* — Kilpatrick Townsend & Stockton LLP

(57) ABSTRACT

This invention provides fusion proteins comprising a Filovirus glycoprotein segment and an immunoglobulin polypeptide segment. The fusion proteins are useful in immunogenic compositions to protect against infections by Filoviruses, such as Ebola virus, in both humans and non-human animals. The fusion proteins are also useful in diagnostic assays to detect Filovirus infections.

13 Claims, 16 Drawing Sheets

SEQUENCE LISTING

<160> NUMBER OF SEQ ID NOS: 15

<210> SEQ ID NO 1
<211> LENGTH: 3209
<212> TYPE: DNA
<213> ORGANISM: Artificial Sequence
<220> FEATURE:
<223> OTHER INFORMATION: synthetic fusion protein Zaire Ebola virus,
      Mayinga strain glycoprotein extracellular domain segment fused to
      immunoglobulin heavy chain constant domain (Fc fragment) from IgG1
      (ZEBOVgp-Fc) without a linker

<400> SEQUENCE: 1

```
gtcgacagta tgggcgttac aggaatattg cagttacctc gtgatcgatt caagaggaca      60
tcattctttc tttgggtaat tatccttttc caaagaacat tttccatccc acttggagtc     120
atccacaata gcacattaca ggttagtgat gtcgacaaac tagtttgtcg tgacaaactg     180
tcatccacaa atcaattgag atcagttgga ctgaatctcg aagggaatgg agtggcaact     240
gacgtgccat ctgcaactaa agatggggc ttcaggtccg gtgtcccacc aaaggtggtc     300
aattatgaag ctggtgaatg ggctgaaaac tgctacaatc ttgaaatcaa aaaacctgac     360
gggagtgagt gtctaccagc agcgccagac gggattcggg gcttcccccg gtgccggtat     420
gtgcacaaag tatcaggaac gggaccgtgt gccggagact tgccttcca taaagagggt     480 gctttcttcc tgtatgatcg acttgcttcc acagttatct accgaggaac gactttcgct     540
gaaggtgtcg ttgcatttct gatactgccc caagctaaga aggacttctt cagctcacac     600
cccttgagag agccggtcaa tgcaacggag acccgtcta gtggctacta ttctaccaca     660
attagatatc aggctaccgg ttttggaacc aatgagacag agtacttgtt cgaggttgac     720
aatttgacct acgtccaact tgaatcaaga ttcacaccac agtttctgct ccagctgaat     780
gagacaatat atacaagtgg aaaaggagc aataccacgg aaaactaat ttggaaggtc     840 aaccccgaaa ttgatacaac aatcggggag tgggccttct gggaaactaa aaaaaacctc     900
actagaaaaa ttcgcagtga agagttgtct ttcacagttg tatcaaacgg agccaaaaac     960
atcagtggtc agagtccggc gcgaacttct ccgacccag ggaccaacac aacaactgaa    1020
gaccacaaaa tcatggcttc agaaaattcc tctgcaatgg ttcaagtgca cagtcaagga    1080
agggaagctg cagtgtcgca tctaacaacc cttgccacaa tctccacgag tccccaatcc    1140
ctcacaacca aaccaggtcc ggacaacagc acccataata cacccgtgta taaacttgac    1200
atctctgagg caactcaagt tgaacaacat caccgcagaa cagacaacga cagcacagcc    1260
tccgacactc cctctgccac gaccgcagcc ggaccccaa agcagagaa caccaacacg    1320 agcaagagca ctgacttcct ggaccccgcc accacaacaa gtcccaaaa ccacagcgag    1380 accgctggca caacaacac tcatcaccaa gataccggag aagagagtgc cagcagcggg    1440
aagctaggct taattaccaa tactattgct ggagtcgcag gactgatcac aggcgggaga    1500
agaactcgaa gagaagcaat tgtcaatgct caacccaaat gcaaccctaa tttacattac    1560
tggactactc aggatgaagg tgctgcaatc ggactggcct ggataccata tttcgggcca    1620
gcagccgagg gaatttacat agagggcta atgcacaatc aagatggttt aatctgtgg    1680 ttgagacagc tggccaacga gacgactcaa gctcttcaac tgttcctgag agccacaact    1740
gagctacgca ccttttcaat cctcaaccgt aaggcaattg atttcttgct gcagcgatgg    1800
ggcggcacat gccacattct gggaccggac tgctgtatcg aaccacatga ttggaccaag    1860
aacataacag acaaaattga tcagattatt catgattttg ttgataaaac ccttccggac    1920
```

-continued

```
ggtgagtact agttctatcc tgcctggacg catcccggct atgcagtccc agtccagggc    1980
agcaaggcag gccccgtctg cctcttcacc cggaggcctc tgcccgcccc actcatgctc    2040
agggagaggg tcttctggct ttttccccag gctctgggca ggcacaggct aggtgcccct    2100
aacccaggcc ctgcacacaa aggggcaggt gctgggctca gacctgccaa gagccatatc    2160
cgggaggacc ctgcccctga cctaagccca ccccaaaggc caaactctcc actccctcag    2220
ctcggacacc ttctctcctc ccagattcca gtaactccca atcttctctc tgcagagccc    2280
aaatcttgtg acaaaactca cacatgccca ccgtgcccag gtaagccagc ccaggcctcg    2340
ccctccagct caaggcggga caggtgccct agagtagcct gcatccaggg acaggcccca    2400
gccgggtgct gacacgtcca cctccatctc ttcctcagca cctgaactcc tggggggacc    2460
gtcagtcttc ctcttccccc caaaacccaa ggacaccctc atgatctccc ggacccctga    2520
ggtcacatgc gtggtggtgg acgtgagcca cgaagaccct gaggtcaagt tcaactggta    2580
cgtggacggc gtggaggtgc ataatgccaa gacaaagccg cgggaggagc agtacaacag    2640
cacgtaccgt gtggtcagcg tcctcaccgt cctgcaccag gactggctga atggcaagga    2700
gtacaagtgc aaggtctcca acaaagccct cccagccccc atcgagaaaa ccatctccaa    2760
agccaaaggt gggacccgtg gggtgcgagg gccacatgga cagaggccgg ctcggcccac    2820
cctctgccct gagagtgacc gctgtaccaa cctctgtccc tacagggcag ccccgagaac    2880
cacaggtgta caccctgccc ccatcccggg aggagatgac caagaaccag gtcagcctga    2940
cctgcctggt caaaggcttc tatcccagcg acatcgccgt ggagtgggag agcaatgggc    3000
agccggagaa caactacaag accacgcctc ccgtgctgga ctccgacggc tccttcttcc    3060
tctatagcaa gctcaccgtg gacaagagca ggtggcagca ggggaacgtc ttctcatgct    3120
ccgtgatgca tgaggctctg cacaaccact acacgcagaa gagcctctcc ctgtccccgg    3180
gtaaatccag ctcacaattg tctagatga                                     3209
```

<210> SEQ ID NO 2
<211> LENGTH: 861
<212> TYPE: PRT
<213> ORGANISM: Artificial Sequence
<220> FEATURE:
<223> OTHER INFORMATION: synthetic fusion protein Zaire Ebola virus,
      Mayinga strain glycoprotein extracellular domain segment fused to
      immunoglobulin heavy chain constant domain (Fc fragment) from IgG1
      (ZEBOVgp-Fc) without a linker

<400> SEQUENCE: 2

Met Gly Val Thr Gly Ile Leu Gln Leu Pro Arg Asp Arg Phe Lys Arg
 1               5                  10                  15

Thr Ser Phe Phe Leu Trp Val Ile Ile Leu Phe Gln Arg Thr Phe Ser
            20                  25                  30

Ile Pro Leu Gly Val Ile His Asn Ser Thr Leu Gln Val Ser Asp Val
        35                  40                  45

Asp Lys Leu Val Cys Arg Asp Lys Leu Ser Ser Thr Asn Gln Leu Arg
    50                  55                  60

Ser Val Gly Leu Asn Leu Glu Gly Asn Gly Val Ala Thr Asp Val Pro
65                  70                  75                  80

Ser Ala Thr Lys Arg Trp Gly Phe Arg Ser Gly Val Pro Pro Lys Val
                85                  90                  95

Val Asn Tyr Glu Ala Gly Glu Trp Ala Glu Asn Cys Tyr Asn Leu Glu
            100                 105                 110

Ile Lys Lys Pro Asp Gly Ser Glu Cys Leu Pro Ala Ala Pro Asp Gly

-continued

```
            115                 120                 125
Ile Arg Gly Phe Pro Arg Cys Arg Tyr Val His Lys Val Ser Gly Thr
130                 135                 140
Gly Pro Cys Ala Gly Asp Phe Ala Phe His Lys Glu Gly Ala Phe Phe
145                 150                 155                 160
Leu Tyr Asp Arg Leu Ala Ser Thr Val Ile Tyr Arg Gly Thr Thr Phe
                165                 170                 175
Ala Glu Gly Val Val Ala Phe Leu Ile Leu Pro Gln Ala Lys Lys Asp
                180                 185                 190
Phe Phe Ser Ser His Pro Leu Arg Glu Pro Val Asn Ala Thr Glu Asp
                195                 200                 205
Pro Ser Ser Gly Tyr Tyr Ser Thr Thr Ile Arg Tyr Gln Ala Thr Gly
        210                 215                 220
Phe Gly Thr Asn Glu Thr Glu Tyr Leu Phe Glu Val Asp Asn Leu Thr
225                 230                 235                 240
Tyr Val Gln Leu Glu Ser Arg Phe Thr Pro Gln Phe Leu Leu Gln Leu
                245                 250                 255
Asn Glu Thr Ile Tyr Thr Ser Gly Lys Arg Ser Asn Thr Thr Gly Lys
                260                 265                 270
Leu Ile Trp Lys Val Asn Pro Glu Ile Asp Thr Thr Ile Gly Glu Trp
                275                 280                 285
Ala Phe Trp Glu Thr Lys Lys Asn Leu Thr Arg Lys Ile Arg Ser Glu
                290                 295                 300
Glu Leu Ser Phe Thr Val Val Ser Asn Gly Ala Lys Asn Ile Ser Gly
305                 310                 315                 320
Gln Ser Pro Ala Arg Thr Ser Ser Asp Pro Gly Thr Asn Thr Thr Thr
                        325                 330                 335
Glu Asp His Lys Ile Met Ala Ser Glu Asn Ser Ser Ala Met Val Gln
                340                 345                 350
Val His Ser Gln Gly Arg Glu Ala Ala Val Ser His Leu Thr Thr Leu
        355                 360                 365
Ala Thr Ile Ser Thr Ser Pro Gln Ser Leu Thr Thr Lys Pro Gly Pro
370                 375                 380
Asp Asn Ser Thr His Asn Thr Pro Val Tyr Lys Leu Asp Ile Ser Glu
385                 390                 395                 400
Ala Thr Gln Val Glu Gln His Arg Arg Thr Asp Asn Asp Ser Thr
                405                 410                 415
Ala Ser Asp Thr Pro Ser Ala Thr Thr Ala Ala Gly Pro Pro Lys Ala
                420                 425                 430
Glu Asn Thr Asn Thr Ser Lys Ser Thr Asp Phe Leu Asp Pro Ala Thr
                435                 440                 445
Thr Thr Ser Pro Gln Asn His Ser Glu Thr Ala Gly Asn Asn Asn Thr
        450                 455                 460
His His Gln Asp Thr Gly Glu Glu Ser Ala Ser Ser Gly Lys Leu Gly
465                 470                 475                 480
Leu Ile Thr Asn Thr Ile Ala Gly Val Ala Gly Leu Ile Thr Gly Gly
                485                 490                 495
Arg Arg Thr Arg Arg Glu Ala Ile Val Asn Ala Gln Pro Lys Cys Asn
                500                 505                 510
Pro Asn Leu His Tyr Trp Thr Thr Gln Asp Glu Gly Ala Ala Ile Gly
                515                 520                 525
Leu Ala Trp Ile Pro Tyr Phe Gly Pro Ala Ala Glu Gly Ile Tyr Ile
                530                 535                 540
```

Glu Gly Leu Met His Asn Gln Asp Gly Leu Ile Cys Gly Leu Arg Gln
545                 550                 555                 560

Leu Ala Asn Glu Thr Thr Gln Ala Leu Gln Leu Phe Leu Arg Ala Thr
                565                 570                 575

Thr Glu Leu Arg Thr Phe Ser Ile Leu Asn Arg Lys Ala Ile Asp Phe
            580                 585                 590

Leu Leu Gln Arg Trp Gly Gly Thr Cys His Ile Leu Gly Pro Asp Cys
        595                 600                 605

Cys Ile Glu Pro His Asp Trp Thr Lys Asn Ile Thr Asp Lys Ile Asp
    610                 615                 620

Gln Ile Ile His Asp Phe Val Asp Lys Thr Leu Pro Asp Gly Thr Cys
625                 630                 635                 640

Pro Pro Cys Pro Ala Pro Glu Leu Leu Gly Gly Pro Ser Val Phe Leu
                645                 650                 655

Phe Pro Pro Lys Pro Lys Asp Thr Leu Met Ile Ser Arg Thr Pro Glu
            660                 665                 670

Val Thr Cys Val Val Val Asp Val Ser His Glu Asp Pro Glu Val Lys
        675                 680                 685

Phe Asn Trp Tyr Val Asp Gly Val Glu Val His Asn Ala Lys Thr Lys
    690                 695                 700

Pro Arg Glu Glu Gln Tyr Asn Ser Thr Tyr Arg Val Val Ser Val Leu
705                 710                 715                 720

Thr Val Leu His Gln Asp Trp Leu Asn Gly Lys Glu Tyr Lys Cys Lys
                725                 730                 735

Val Ser Asn Lys Ala Leu Pro Ala Pro Ile Glu Lys Thr Ile Ser Lys
            740                 745                 750

Ala Lys Gly Gln Pro Arg Glu Pro Gln Val Tyr Thr Leu Pro Pro Ser
        755                 760                 765

Arg Asp Glu Leu Thr Lys Asn Gln Val Ser Leu Thr Cys Leu Val Lys
    770                 775                 780

Gly Phe Tyr Pro Ser Asp Ile Ala Val Glu Trp Glu Ser Asn Gly Gln
785                 790                 795                 800

Pro Glu Asn Asn Tyr Lys Thr Thr Pro Pro Val Leu Asp Ser Asp Gly
                805                 810                 815

Pro Phe Phe Leu Tyr Ser Lys Leu Thr Val Asp Lys Ser Arg Trp Gln
            820                 825                 830

Gln Gly Asn Val Phe Ser Cys Ser Val Met His Glu Ala Leu His Asn
        835                 840                 845

His Tyr Thr Gln Lys Ser Leu Ser Leu Ser Pro Gly Lys
    850                 855                 860

<210> SEQ ID NO 3
<211> LENGTH: 3244
<212> TYPE: DNA
<213> ORGANISM: Artificial Sequence
<220> FEATURE:
<223> OTHER INFORMATION: synthetic fusion protein Zaire Ebola virus,
      Mayinga strain glycoprotein extracellular domain segment fused to
      immunoglobulin heavy chain constant domain (Fc fragment) from IgG1
      (ZEBOVgp-Fc) with a FLAG tag linker

<400> SEQUENCE: 3
gtcgacagta tgggcgttac aggaatattg cagttacctc gtgatcgatt caagaggaca      60
tcattctttc tttgggtaat tatcctttc caaagaacat tttccatccc acttggagtc     120
atccacaata gcacattaca ggttagtgat gtcgacaaac tagtttgtcg tgacaaactg    180

```
tcatccacaa atcaattgag atcagttgga ctgaatctcg aagggaatgg agtggcaact        240
gacgtgccat ctgcaactaa aagatggggc ttcaggtccg gtgtcccacc aaaggtggtc        300
aattatgaag ctggtgaatg ggctgaaaac tgctacaatc ttgaaatcaa aaaacctgac        360
gggagtgagt gtctaccagc agcgcagacg ggattcgggg cttcccccgg tgccggtatg        420
tgcacaaagt atcaggaacg ggaccgtgtg ccggagactt tgccttccat aaagagggtg        480
ctttcttcct gtatgatcga cttgcttcca cagttatcta ccgaggaacg actttcgctg        540
aaggtgtcgt tgcatttctg atactgcccc aagctaagaa ggacttcttc agctcacacc        600
ccttgagaga gccggtcaat gcaacggagg acccgtctag tggctactat tctaccacaa        660
ttagatatca ggctaccggt tttggaacca atgagacaga gtacttgttc gaggttgaca        720
atttgaccta cgtccaactt gaatcaagat tcacaccaca gtttctgctc cagctgaatg        780
agacaatata tacaagtggg aaaaggagca ataccacggg aaaactaatt tggaaggtca        840
accccgaaat tgatacaaca atcggggagt gggccttctg ggaaactaaa aaaaacctca        900
ctagaaaaat tcgcagtgaa gagttgtctt tcacagttgt atcaaacgga gccaaaaaca        960
tcagtggtca gagtccggcg cgaacttctt ccgacccagg gaccaacaca caactgaag       1020 accacaaaat catggcttca gaaaattcct ctgcaatggt tcaagtgcac agtcaaggaa       1080
gggaagctgc agtgtcgcat ctaacaaccc ttgccacaat ctccacgagt ccccaatccc       1140
tcacaaccaa accaggtccg gacaacagca cccataatac acccgtgtat aaacttgaca       1200
tctctgaggc aactcaagtt gaacaacatc accgcagaac agacaacgac agcacagcct       1260
ccgacactcc ctctgccacg accgcagccg gaccccaaa agcagagaac accaacacga       1320
gcaagagcac tgacttcctg gaccccgcca ccacaacaag tccccaaaac cacagcgaga       1380
ccgctggcaa caacaacact catcaccaag ataccggaga agagagtgcc agcagcggga       1440
agctaggctt aattaccaat actattgctg gagtcgcagg actgatcaca ggcgggagaa       1500
gaactcgaag agaagcaatt gtcaatgctc aacccaaatg caacccctaat ttacattact       1560 ggactactca ggatgaaggt gctgcaatcg gactggcctg gataccatat ttcgggccag       1620
cagccgaggg aatttacata gagggctaa tgcacaatca agatggttta atctgtgggt       1680
tgagacagct ggccaacgag acgactcaag ctcttcaact gttcctgaga gccacaactg       1740
agctacgcac ctttttcaatc ctcaaccgta aggcaattga tttcttgctg cagcgatggg       1800
gcggcacatg ccacattctg ggaccggact gctgtatcga accacatgat tggaccaaga       1860
acataacaga caaaattgat cagattattc atgatttgt tgataaaacc cttcccggacg       1920 gcggtggaga ctacaaggac gacgatgaca agggaggtga gtactagttc tatcctgcct       1980
ggacgcatcc cggctatgca gtcccagtcc agggcagcaa gcaggcccc gtctgcctct       2040 tcacccggag gcctctgccc gccccactca tgctcaggga gagggtcttc tggctttttc       2100
cccaggctct gggcaggcac aggctaggtg ccctaacccc aggccctgca cacaaagggg       2160
caggtgctgg gctcagacct gccaagagcc atatccggga ggaccctgcc cctgacctaa       2220
gcccacccca aaggccaaac tctccactcc ctcagctcgg acaccttctc tcctcccaga       2280
ttccagtaac tcccaatctt ctctctgcag agcccaaatc ttgtgacaaa actcacacat       2340
gcccaccgtg cccaggtaag ccagcccagg cctcgccctc cagctcaagg cgggacaggt       2400
gccctagagt agcctgcatc cagggacagg ccccagccgg tgctgacac gtccacctcc       2460 atctcttcct cagcacctga actcctgggg ggaccgtcag tcttcctctt ccccccaaaa       2520
```

```
cccaaggaca ccctcatgat ctcccggacc cctgaggtca catgcgtggt ggtggacgtg    2580
agccacgaag accctgaggt caagttcaac tggtacgtgg acggcgtgga ggtgcataat    2640
gccaagacaa agccgcggga ggagcagtac aacagcacgt accgtgtggt cagcgtcctc    2700
accgtcctgc accaggactg gctgaatggc aaggagtaca agtgcaaggt ctccaacaaa    2760
gccctcccag cccccatcga aaaaccatc tccaaagcca aggtgggac ccgtggggtg    2820 cgagggccac atggacagag gccggctcgg cccaccctct gccctgagag tgaccgctgt    2880
accaacctct gtccctacag ggcagccccg agaaccacag gtgtacaccc tgcccccatc    2940 ccggaggag atgaccaaga accaggtcag cctgacctgc ctggtcaaag gcttctatcc    3000
cagcgacatc gccgtggagt gggagagcaa tgggcagccg gagaacaact acaagaccac    3060
gcctcccgtg ctggactccg acggctcctt cttcctctat agcaagctca ccgtggacaa    3120
gagcaggtgg cagcagggga acgtcttctc atgctccgtg atgcatgagg ctctgcacaa    3180
ccactacacg cagaagagcc tctccctgtc cccgggtaaa tccagctcac aattgtctag    3240
atga                                                                3244
```

<210> SEQ ID NO 4
<211> LENGTH: 870
<212> TYPE: PRT
<213> ORGANISM: Artificial Sequence
<220> FEATURE:
<223> OTHER INFORMATION: synthetic fusion protein Zaire Ebola virus, Mayinga strain glycoprotein extracellular domain segment fused to immunoglobulin heavy chain constant domain (Fc fragment) from IgG1 (ZEBOVgp-Fc) with a FLAG tag linker

<400> SEQUENCE: 4

```
Met Gly Val Thr Gly Ile Leu Gln Leu Pro Arg Asp Arg Phe Lys Arg
1               5                   10                  15

Thr Ser Phe Phe Leu Trp Val Ile Ile Leu Phe Gln Arg Thr Phe Ser
            20                  25                  30

Ile Pro Leu Gly Val Ile His Asn Ser Thr Leu Gln Val Ser Asp Val
        35                  40                  45

Asp Lys Leu Val Cys Arg Asp Lys Leu Ser Ser Thr Asn Gln Leu Arg
    50                  55                  60

Ser Val Gly Leu Asn Leu Glu Gly Asn Gly Val Ala Thr Asp Val Pro
65                  70                  75                  80

Ser Ala Thr Lys Arg Trp Gly Phe Arg Ser Gly Val Pro Pro Lys Val
                85                  90                  95

Val Asn Tyr Glu Ala Gly Glu Trp Ala Glu Asn Cys Tyr Asn Leu Glu
            100                 105                 110

Ile Lys Lys Pro Asp Gly Ser Glu Cys Leu Pro Ala Ala Pro Asp Gly
        115                 120                 125

Ile Arg Gly Phe Pro Arg Cys Arg Tyr Val His Lys Val Ser Gly Thr
    130                 135                 140

Gly Pro Cys Ala Gly Asp Phe Ala Phe His Lys Glu Gly Ala Phe Phe
145                 150                 155                 160

Leu Tyr Asp Arg Leu Ala Ser Thr Val Ile Tyr Arg Gly Thr Thr Phe
                165                 170                 175

Ala Glu Gly Val Val Ala Phe Leu Ile Leu Pro Gln Ala Lys Lys Asp
            180                 185                 190

Phe Phe Ser Ser His Pro Leu Arg Glu Pro Val Asn Ala Thr Glu Asp
        195                 200                 205

Pro Ser Ser Gly Tyr Tyr Ser Thr Thr Ile Arg Tyr Gln Ala Thr Gly
```

-continued

```
                210                 215                 220
Phe Gly Thr Asn Glu Thr Glu Tyr Leu Phe Glu Val Asp Asn Leu Thr
225                 230                 235                 240

Tyr Val Gln Leu Glu Ser Arg Phe Thr Pro Gln Phe Leu Leu Gln Leu
                245                 250                 255

Asn Glu Thr Ile Tyr Thr Ser Gly Lys Arg Ser Asn Thr Thr Gly Lys
                260                 265                 270

Leu Ile Trp Lys Val Asn Pro Glu Ile Asp Thr Thr Ile Gly Glu Trp
                275                 280                 285

Ala Phe Trp Glu Thr Lys Lys Asn Leu Thr Arg Lys Ile Arg Ser Glu
                290                 295                 300

Glu Leu Ser Phe Thr Val Val Ser Asn Gly Ala Lys Asn Ile Ser Gly
305                 310                 315                 320

Gln Ser Pro Ala Arg Thr Ser Ser Asp Pro Gly Thr Asn Thr Thr Thr
                325                 330                 335

Glu Asp His Lys Ile Met Ala Ser Glu Asn Ser Ser Ala Met Val Gln
                340                 345                 350

Val His Ser Gln Gly Arg Glu Ala Ala Val Ser His Leu Thr Thr Leu
                355                 360                 365

Ala Thr Ile Ser Thr Ser Pro Gln Ser Leu Thr Thr Lys Pro Gly Pro
                370                 375                 380

Asp Asn Ser Thr His Asn Thr Pro Val Tyr Lys Leu Asp Ile Ser Glu
385                 390                 395                 400

Ala Thr Gln Val Glu Gln His His Arg Arg Thr Asp Asn Asp Ser Thr
                405                 410                 415

Ala Ser Asp Thr Pro Ser Ala Thr Thr Ala Ala Gly Pro Pro Lys Ala
                420                 425                 430

Glu Asn Thr Asn Thr Ser Lys Ser Thr Asp Phe Leu Asp Pro Ala Thr
                435                 440                 445

Thr Thr Ser Pro Gln Asn His Ser Glu Thr Ala Gly Asn Asn Asn Thr
                450                 455                 460

His His Gln Asp Thr Gly Glu Glu Ser Ala Ser Ser Gly Lys Leu Gly
465                 470                 475                 480

Leu Ile Thr Asn Thr Ile Ala Gly Val Ala Gly Leu Ile Thr Gly Gly
                485                 490                 495

Arg Arg Thr Arg Arg Glu Ala Ile Val Asn Ala Gln Pro Lys Cys Asn
                500                 505                 510

Pro Asn Leu His Tyr Trp Thr Thr Gln Asp Glu Gly Ala Ala Ile Gly
                515                 520                 525

Leu Ala Trp Ile Pro Tyr Phe Gly Pro Ala Ala Glu Gly Ile Tyr Ile
530                 535                 540

Glu Gly Leu Met His Asn Gln Asp Gly Leu Ile Cys Gly Leu Arg Gln
545                 550                 555                 560

Leu Ala Asn Glu Thr Thr Gln Ala Leu Gln Leu Phe Leu Arg Ala Thr
                565                 570                 575

Thr Glu Leu Arg Thr Phe Ser Ile Leu Asn Arg Lys Ala Ile Asp Phe
                580                 585                 590

Leu Leu Gln Arg Trp Gly Gly Thr Cys His Ile Leu Gly Pro Asp Cys
                595                 600                 605

Cys Ile Glu Pro His Asp Trp Thr Lys Asn Ile Thr Asp Lys Ile Asp
610                 615                 620

Gln Ile Ile His Asp Phe Val Asp Lys Thr Leu Pro Asp Asp Tyr Lys
625                 630                 635                 640
```

Asp Asp Asp Asp Lys Gly Gly Thr Cys Pro Pro Cys Pro Ala Pro Glu
             645                 650                 655

Leu Leu Gly Gly Pro Ser Val Phe Leu Phe Pro Pro Lys Pro Lys Asp
         660                 665                 670

Thr Leu Met Ile Ser Arg Thr Pro Glu Val Thr Cys Val Val Val Asp
     675                 680                 685

Val Ser His Glu Asp Pro Glu Val Lys Phe Asn Trp Tyr Val Asp Gly
 690                 695                 700

Val Glu Val His Asn Ala Lys Thr Lys Pro Arg Glu Glu Gln Tyr Asn
705                 710                 715                 720

Ser Thr Tyr Arg Val Val Ser Val Leu Thr Val Leu His Gln Asp Trp
                 725                 730                 735

Leu Asn Gly Lys Glu Tyr Lys Cys Lys Val Ser Asn Lys Ala Leu Pro
             740                 745                 750

Ala Pro Ile Glu Lys Thr Ile Ser Lys Ala Lys Gly Gln Pro Arg Glu
         755                 760                 765

Pro Gln Val Tyr Thr Leu Pro Pro Ser Arg Asp Glu Leu Thr Lys Asn
770                 775                 780

Gln Val Ser Leu Thr Cys Leu Val Lys Gly Phe Tyr Pro Ser Asp Ile
785                 790                 795                 800

Ala Val Glu Trp Glu Ser Asn Gly Gln Pro Glu Asn Asn Tyr Lys Thr
                 805                 810                 815

Thr Pro Pro Val Leu Asp Ser Asp Gly Pro Phe Phe Leu Tyr Ser Lys
             820                 825                 830

Leu Thr Val Asp Lys Ser Arg Trp Gln Gln Gly Asn Val Phe Ser Cys
         835                 840                 845

Ser Val Met His Glu Ala Leu His Asn His Tyr Thr Gln Lys Ser Leu
     850                 855                 860

Ser Leu Ser Pro Gly Lys
865                 870

<210> SEQ ID NO 5
<211> LENGTH: 36
<212> TYPE: DNA
<213> ORGANISM: Artificial Sequence
<220> FEATURE:
<223> OTHER INFORMATION: synthetic PCR amplification oligonucleotide
      GP/SalI

<400> SEQUENCE: 5
gtcgacagta tgggcgttac aggaatattg cagtta                            36

<210> SEQ ID NO 6
<211> LENGTH: 73
<212> TYPE: DNA
<213> ORGANISM: Artificial Sequence
<220> FEATURE:
<223> OTHER INFORMATION: synthetic PCR amplification oligonucleotide
      GP/Flag/SpeI

<400> SEQUENCE: 6
actagtactc acctcccttg tcatcgtcgt ccttgtagtc tccaccgccg tccggaaggg    60
ttttatcaac aaa                                                      73

<210> SEQ ID NO 7
<211> LENGTH: 8
<212> TYPE: PRT
<213> ORGANISM: Artificial Sequence -continued

```
<220> FEATURE:
<223> OTHER INFORMATION: synthetic FLAG tag peptide

<400> SEQUENCE: 7

Asp Thr Lys Asp Asp Asp Asp Lys
 1               5

<210> SEQ ID NO 8
<211> LENGTH: 73
<212> TYPE: DNA
<213> ORGANISM: Artificial Sequence
<220> FEATURE:
<223> OTHER INFORMATION: synthetic PCR amplification oligonucleotide
      SP/Flag/SpeI

<400> SEQUENCE: 8
actagtactc acctcccttg tcatcgtcgt ccttgtagtc tccaccgccg gaaaatgttc      60
tttggaaaag gat                                                        73

<210> SEQ ID NO 9
<211> LENGTH: 36
<212> TYPE: DNA
<213> ORGANISM: Artificial Sequence
<220> FEATURE:
<223> OTHER INFORMATION: synthetic PCR amplification oligonucleotide
      GP/NheI(+)

<400> SEQUENCE: 9
actagtagta tgggcgttac aggaatattg cagtta                               36

<210> SEQ ID NO 10
<211> LENGTH: 33
<212> TYPE: DNA
<213> ORGANISM: Artificial Sequence
<220> FEATURE:
<223> OTHER INFORMATION: synthetic PCR amplification oligonucleotide
      GP/NheI(-)

<400> SEQUENCE: 10
gctagcctaa aagacaaatt tgcatataca gaa                                  33

<210> SEQ ID NO 11
<211> LENGTH: 9
<212> TYPE: PRT
<213> ORGANISM: Artificial Sequence
<220> FEATURE:
<223> OTHER INFORMATION: synthetic Ebola virus (EBOV) glycoprotein (GP)
      specific peptide

<400> SEQUENCE: 11

Leu Tyr Asp Arg Leu Ala Ser Thr Val
 1               5

<210> SEQ ID NO 12
<211> LENGTH: 16
<212> TYPE: PRT
<213> ORGANISM: Artificial Sequence
<220> FEATURE:
<223> OTHER INFORMATION: synthetic Ebola virus (EBOV) glycoprotein (GP)
      specific peptide

<400> SEQUENCE: 12

Val Ser Thr Gly Thr Gly Pro Gly Ala Gly Asp Phe Ala Phe His Lys
 1               5                  10                  15

<210> SEQ ID NO 13
```

```
<211> LENGTH: 9
<212> TYPE: PRT
<213> ORGANISM: Artificial Sequence
<220> FEATURE:
<223> OTHER INFORMATION: synthetic Ebola virus (EBOV) glycoprotein (GP)
      specific peptide

<400> SEQUENCE: 13

Glu Tyr Leu Phe Glu Val Asp Asn Leu
 1               5

<210> SEQ ID NO 14
<211> LENGTH: 8
<212> TYPE: PRT
<213> ORGANISM: Artificial Sequence
<220> FEATURE:
<223> OTHER INFORMATION: synthetic unrelated peptide negative control

<400> SEQUENCE: 14

Lys Ile Asn Ser Thr Ala Leu Leu
 1               5

<210> SEQ ID NO 15
<211> LENGTH: 24
<212> TYPE: DNA
<213> ORGANISM: Artificial Sequence
<220> FEATURE:
<223> OTHER INFORMATION: synthetic FLAG tag and enterokinase protease
      restriction site

<400> SEQUENCE: 15
gactacaagg acgacgatga caag                                              24
```

FUSION PROTEIN COMPRISING THE EXTRACELLULAR DOMAIN OF A FILOVIRUS GLYCOPROTEIN FUSED TO AN IMMUNOGLOBULIN HEAVY CHAIN CONSTANT REGION

PRIORITY

The present application is a U.S. National Phase of PCT/US2011/058418, filed Oct. 28, 2011, which claims the benefit of U.S. Provisional Application No. 61/407,842, filed on Oct. 28, 2010, the entire contents of which are incorporated by reference herein in their entirety.

REFERENCE TO SEQUENCE LISTING

This application includes a Sequence Listing as a text file named "77867-596100US-874026_SEQLIST.txt" created Apr. 26, 2013, and containing 26,475 bytes. The material contained in this text file is incorporated by reference in its entirety for all purposes.

FIELD OF THE INVENTION

This invention relates to the use of Filovirus glycoprotein fusion proteins for the prevention and diagnosis of Filovirus infection.

BACKGROUND OF THE INVENTION

Ebola virus (EBOV) and Marburgvirus (MARV) are members of the Filoviridae, a family of viruses classified as "Category A" bioterrorism agents that cause severe hemorrhagic fever in humans and nonhuman primates with high morbidity and mortality rates up to 90% (Sanchez et al., Filoviridae: Marburg and Ebola viruses, p. 1409-1448. In D. M. Knipe, P. M. Howley, D. E. Griffin, M. A. Martin, R. A. Lamb, B. Roizman, and S. E. Straus (ed.), Fields Virology, 5th ed. Philadelphia, Pa.: Lippincott Williams & Wilkins, 2007). After a short incubation period of 4 to 10 days, Filovirus-infected individuals develop an abrupt onset of symptoms that include fever, chills, malaise, and myalgia that are common to many other viral infections. MARV is antigenically stable and exists in only one species, whereas EBOV is more variable and has five species. The Bundibugyo EBOV emerged recently in late 2007 outbreak in Uganda (Towner et al., PLoS Pathog 2008 November; 4(11):e1000212), and is more related to the Ivory Coast than to the Zaire, Sudan, or Reston EBOV species. Zaire EBOV (ZEBOV) is typically associated with the highest lethality. The increased number of outbreaks in Africa and the recent EBOV outbreak in pigs (Normile Science 2009 Jan. 23; 323(5913):451), which raised concerns that livestock could transmit the deadly disease to humans, highlighted the urgency for the development of vaccines and rapid diagnostic tests to contain outbreaks. Vaccines based on the Filovirus glycoprotein (GP) are in preclinical and clinical evaluation, and currently there are no therapeutic agents to treat Filovirus infection. Since licensing of safe and effective Filovirus vaccine could take several more years, diagnosis and quarantine of infected individuals is currently the main tool to limit outbreaks.

Several Filovirus vaccine candidates are currently being developed, including recombinant adenovirus expressing the EBOV GP (Sullivan et al., PLoS Med 2006 June; 3(6):e177; Sullivan et al., Nature 2003 Aug. 7; 424(6949):681-4; and Sullivan et al., Nature 2000 Nov. 30; 408(6812):605-9), recombinant parainfluenza virus (Bukreyev et al., J Virol 2007 June; 81(12):6379-88), recombinant Venezuelan equine encephalitis virus (Pushko et al., Vaccine 2000 Aug. 15; 19(1):142-53), recombinant replication-competent (Feldmann et al., PLoS Pathog 2007 January; 3(1):e2 and Jones et al., Nat Med 2005 July; 11(7):786-90) and -deficient (Halfmann et al., J Virol 2009 April; 83(8):3810-5) vesicular stomatitis virus, and virus-like particles carrying the Filovirus GP (Warfield et al., Proc Natl Acad Sci USA 2003 Dec. 23; 100(26):15889-94 and Warfield et al., J Infect Dis 2007 Nov. 15; 196 Suppl 2:S430-7). Initial studies using baculovirus-expressed Filovirus GP showed partial protection, which could be attributed to the nature of the glycosylation and processing of GP in insect cells (Mellquist-Riemenschneider et al., Virus Res 2003 April; 92(2):187-93).

Despite advances in this regard, a need exists to develop new vaccines against Filoviruse infections. The present invention addresses these and other needs.

BRIEF SUMMARY OF THE INVENTION

This invention provides fusion proteins comprising a Filovirus glycoprotein segment and an immunoglobulin polypeptide segment. In the typical embodiment, the Filovirus glycoprotein segment is an extracellular domain, for example, from an Ebola virus, particularly, the Zaire Ebola virus, Mayinga strain. The immunoglobulin polypeptide segment can be an immunoglobulin heavy chain constant domain polypeptide from IgG1 (e.g., an Fc fragment). In some embodiments, the fusion protein may further comprise a linker between the Filovirus glycoprotein segment and the immunoglobulin polypeptide segment. An exemplary fusion protein of the invention is encoded by a nucleic acid sequence as shown in SEQ ID NO:1 without a linker and SEQ ID NO:3 with a FLAG tag linker.

The invention further provides immunogenic compositions comprising the fusion protein of the invention. The immunogenic composition may further comprise an adjuvant.

Also provided are nucleic acid vectors comprising a nucleic acid sequence encoding a fusion protein of the invention. An exemplary nucleic acid sequence is shown in SEQ ID NO: 1.

The invention further provides methods of inducing a protective immune response against Filovirus infection in a patient. The methods comprise administering to the patient an immunologically effective amount of the immunogenic composition of the invention. The immunogenic composition can comprise the fusion proteins of the invention or nucleic acid molecules encoding them. The composition can be administered by any of a number of routes. In some embodiments, the composition is administered intramuscularly.

The invention also provides methods of detecting an immune response against Filovirus in a patient. The methods include contacting a biological sample from the patient with the fusion protein of the invention and detecting either a humoral or a cellular immune response. Antibodies can be detected using ELISA, chemiluminescence assays, or fluorescence assays. A cellular immune response can be detected by detecting IFN-γ, TNF-α, or other cytokines and cell activation and proliferation assays.

Yet another aspect of the invention are methods of detecting ant-Filovirus antibodies (e.g., neutralizing antibodies) in a biological sample from a patient immunized with Filovirus glycoprotein Fc fusion proteins or other immunogens. Such methods comprise contacting the biological sample with a recombinant Vesicular Stomatitis Virus (VSV) expressing a Filovirus GP (e.g., a Zaire Ebola virus, Mayinga strain) and assessing residual infectivity in a cell susceptible to Filovirus infection. The cells used in the assay can be Vero E6 cells. Alternatively the recombinant VSV particles can be immobilized on a solid support and anti-Filovirus antibodies can be detected using standard methods, such as ELISA, chemiluminescence assays, or fluorescence assays.

DEFINITIONS

The terms "adjuvant" and "immune stimulant" are used interchangeably herein, and are defined as one or more substances that cause stimulation of the immune system. In this context, an adjuvant is used to enhance an immune response to the fusion proteins of the invention.

The terms "amino-terminal" (or "N-terminal") and "carboxyl-terminal" (or "C-terminal") are used herein to denote positions within polypeptides, particularly fusion proteins of the invention. Where the context allows, these terms are used with reference to a particular sequence or segment of a polypeptide or protein to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

The term "corresponding to", when applied to positions of amino acid residues in sequences, means corresponding positions in a plurality of sequences when the sequences are optimally aligned.

The term "expression vector" refers to a linear or circular DNA molecule that comprises a segment encoding a polypeptide of interest (e.g., a fusion protein of the invention) operably linked to additional segments that provide for its transcription. Such additional segments include promoter and terminator sequences, and may also include one or more origins of replication, one or more selectable markers, an enhancer, a polyadenylation signal, and the like. Expression vectors are generally derived from bacterial or viral DNA, and may contain elements of both.

The terms "identical" or percent "identity," in the context of two or more nucleic acids or polypeptide sequences, (e.g., fusion proteins of the invention and polynucleotides that encode them) refer to two or more sequences or subsequences that are the same or have a specified percentage of amino acid residues or nucleotides that are the same, when compared and aligned for maximum correspondence, as measured using one of the following sequence comparison algorithms or by visual inspection.

The phrase "substantially identical," in the context of two nucleic acids or polypeptides of the invention, refers to two or more sequences or subsequences that have at least 60%, more preferably 65%, even more preferably 70%, still more preferably 75%, even more preferably 80%, and most preferably 90-95% nucleotide or amino acid residue identity, when compared and aligned for maximum correspondence, as measured using one of the following sequence comparison algorithms or by visual inspection. Preferably, the substantial identity exists over a region of the sequences that is at least about 50 residues in length, more preferably over a region of at least about 100 residues, and most preferably the sequences are substantially identical over at least about 150 residues. In a most preferred embodiment, the sequences are substantially identical over the entire length of the coding regions.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, *Current Protocols in Molecular Biology*, F. M. Ausubel et al., eds., Current Protocols, a joint venture between Greene Publishing Associates, Inc. and John Wiley & Sons, Inc., (1995 Supplement) (Ausubel)).

Examples of algorithms that are suitable for determining percent sequence identity and sequence similarity are the BLAST and BLAST 2.0 algorithms, which are described in Altschul et al. (1990) *J. Mol. Biol.* 215: 403-410 and Altschuel et al. (1977) *Nucleic Acids Res.* 25: 3389-3402, respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89:10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences or polypeptides of the invention are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions, as described below.

An "immunoglobulin" is a serum protein which functions as an antibody in vertebrate organisms. Each immunoglobulin comprises a light chain and a heavy chain. Each chain comprises a constant domain and a variable domain. There are five types of heavy chain, denoted by α, β, ε, γ, and μ, which defines the class of antibody, IgA, IgD, IgE, IgG, and IgM, respectively. In humans, IgG consists of four subclasses, designated IgG1, IgG2, IgG3, and IgG4. DNA sequences encoding human and non-human immunoglobulin chains are well known in the art.

The term "immunoglobulin heavy chain constant domain polypeptide" denotes a wild-type immunoglobulin heavy chain constant domain or a variant thereof. An IgG constant domain comprises the $C_H1$, $C_H2$, and $C_H3$ domains and the hinge region.

An "Fc fragment" is a fragment of the heavy chain constant domain corresponding to the region of the immunoglobulin that interacts with Fc receptors. In IgG, IgA and IgD, the Fc region corresponds to $C_H2$, and $C_H3$ domains and the hinge region. In IgM and IgE, the Fc regions contain three heavy chain constant domains ($C_H2$, $C_H3$, and $C_H4$).

"Operably linked" indicates that two or more DNA segments are joined together such that they function in concert for their intended purposes. For example, coding sequences are operably linked to promoter in the correct reading frame such that transcription initiates in the promoter and proceeds through the coding segment(s) to the terminator.

A "polynucleotide" is a single- or double-stranded polymer of deoxyribonucleotide or ribonucleotide bases typically read from the 5' to the 3' end. Polynucleotides include RNA and DNA, and may be isolated from natural sources, synthesized in vitro, or prepared from a combination of natural and synthetic molecules. When the term is applied to double-stranded molecules it is used to denote overall length and will be understood to be equivalent to the term "base pairs".

A "polypeptide" is a polymer of amino acid residues joined by peptide bonds, whether produced naturally or synthetically. Polypeptides of less than about 50 amino acid residues are commonly referred to as "oligopeptides".

The term "promoter" is used herein for its art-recognized meaning to denote a portion of a gene containing DNA sequences that provide for the binding of RNA polymerase and initiation of transcription of an operably linked coding sequence. Promoter sequences are typically found in the 5' non-coding regions of genes.

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

The term "substantially similar" in the context of the fusion proteins of the invention indicates that a polypeptide comprises a sequence with at least 90%, preferably at least 95% sequence identity to the reference sequence (e.g., the GP-Fc fusion exemplified here) over a comparison window of 10-20 amino acids. Percentage of sequence identity is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

BRIEF DESCRIPTION OF THE DRAWINGS

FIG. 1 is a schematic representation and purification of the ZEBOVGP-Fc and FLAG-Fc proteins. A) Schematic representation of the fusion proteins. The ZEBOVGP-Fc fusion protein contains the ectodomain of ZEBOV GP tagged at its C terminus with a FLAG peptide and fused to the hinge and Fc regions of human IgG1. The FLAG-Fc fusion protein contains a FLAG tag fused to the hinge and Fc regions of IgG 1. B) SDS-PAGE analysis of fusion proteins. Protein A-purified ZEBOVGP-Fc and FLAG-Fc preparations were analyzed by denaturing SDS-PAGE in a 4-12% gradient gel and stained with Coomassie blue. C) Western blot analysis of ZEBOVGP-Fc and FLAG-Fc. Proteins were resolved by SDS-PAGE under denaturing conditions, transferred to PVDF membranes, and probed with ZEBOV-specific anti-GPI mAb 13F6-1-2, anti-Flag M2 mAb, or goat anti-human Fc Ab. ZEBOV GP 1, GP2-FLAG-Fc, and FLAG-Fc bands are indicated with arrows. Positions and size of molecular weight markers are indicated in kDa.

FIG. 3 shows analysis of anti-ZEBOV GP antibodies in vaccinated C57BL/6 mice. A) Analysis of anti-ZEBOV GP specific antibodies by viral particle ELISA. Mice were vaccinated with ZEBOVGP-Fc or FLAG-Fc and sera samples were obtained 2 weeks after the final vaccination. Sera were titrated on 96-well plates coated with sucrose-purified irradiated ZEBOV particles, rVSV-ZEBOVGP, or control wt VSV.

Figure 2A:
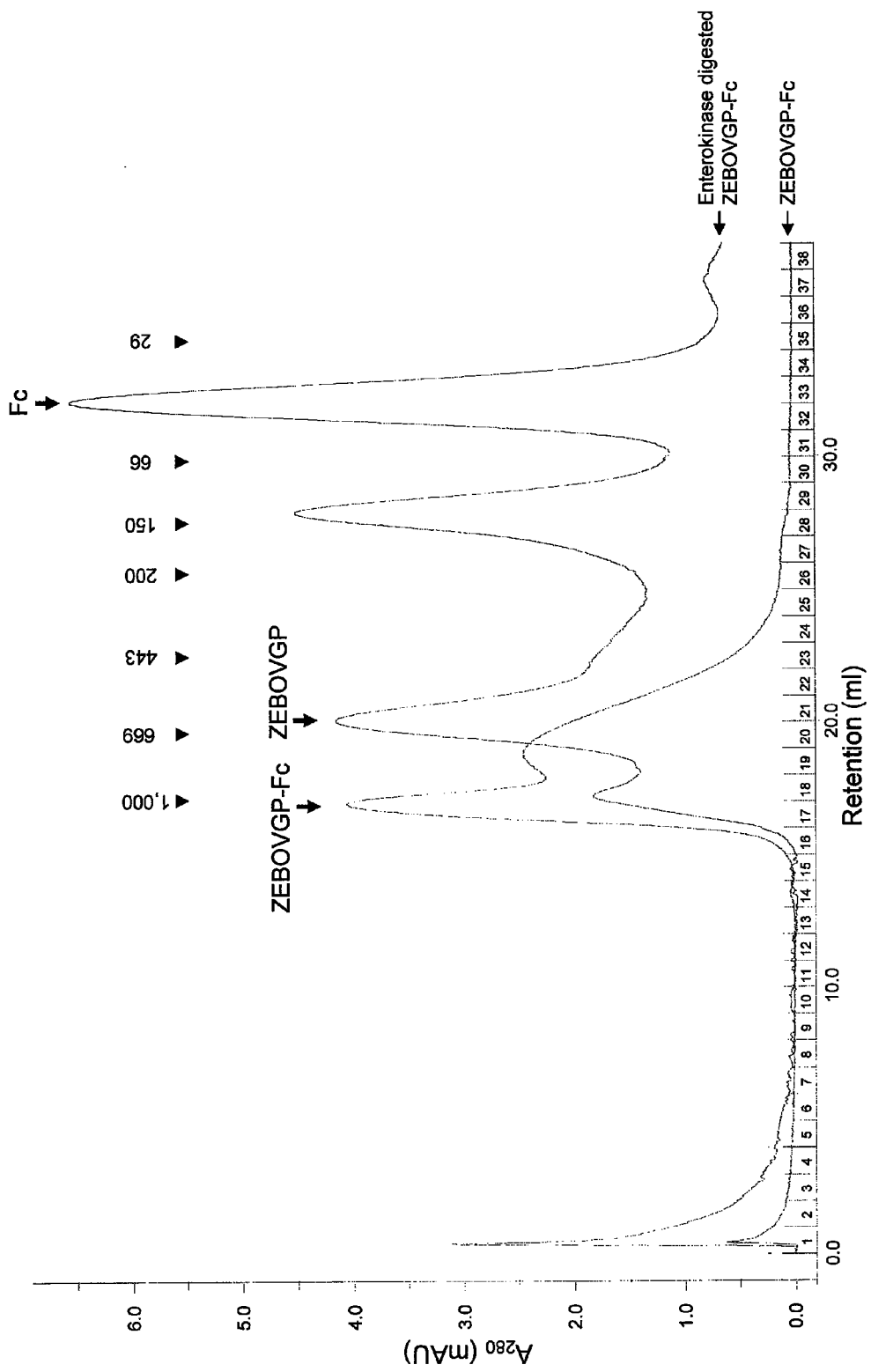
FIG. 2 is a characterization of ZEBOVGP-Fc fusion protein. A) FPLC analysis of protein A-purified ZEBOVGP-Fc. Undigested (gray) or enterokinase-digested (blue) ZEBOVGP-Fc was run on a Superdex 200 size exclusion column under non-denaturing conditions, and absorbance at 280 nm was recorded for each of the 38 collected fractions. Peaks representing ZEBOVGP-Fc, ZEBOV GP, and Fc are marked with arrows. A peak of approximately 150 kDa represents a carrier protein in the enterokinase preparation. The migration of molecular weight standards is shown as arrowheads and their molecular weight is expressed in kDa. B) Western blot analysis of enterokinase-digested ZEBOVGP-Fc protein. Gel filtration peak fractions (20 and 32) were fractionated in denaturing SDS-PAGE, transferred to a PVDF membrane, probed with ZEBOV-specific anti-GP I mAb 13F6-1-2 or goat anti-human anti-Fc antibody. Undigested (U) or enterokinase digested (D) ZEBOVGP-Fc, and FLAG-Fc (Fc) were included in the gel as markers. Arrows indicate the migration of GP1, GP2-FLAG-Fc, and FLAG-Fc. The migration of the molecular weight markers and their sizes are indicated in kDa.

The endpoint dilution titer for each mouse sera is represented as a dot. B) FACS analysis of binding of mouse sera to ZEBOV GP expressed at the cell surface of HEK293-ZEBOVGP cells. HEK293-ZEBOVGP or control vector-transfected HEK293 cells were stained with mouse sera (1 µl) and PE-conjugated goat anti-mouse IgG Ab and analyzed by flow cytometry. The histogram of each mouse sera is shown in a different color, and the histogram of the positive control anti-GP mAb 13F6-1-2 is shown as a dashed grey line. To simplify the graph, the same color was used for sera from two different mice, one vaccinated with ZEBOVGP-Fc (left panels) and the other with FLAG-Fc (right panels).

Figure 4:
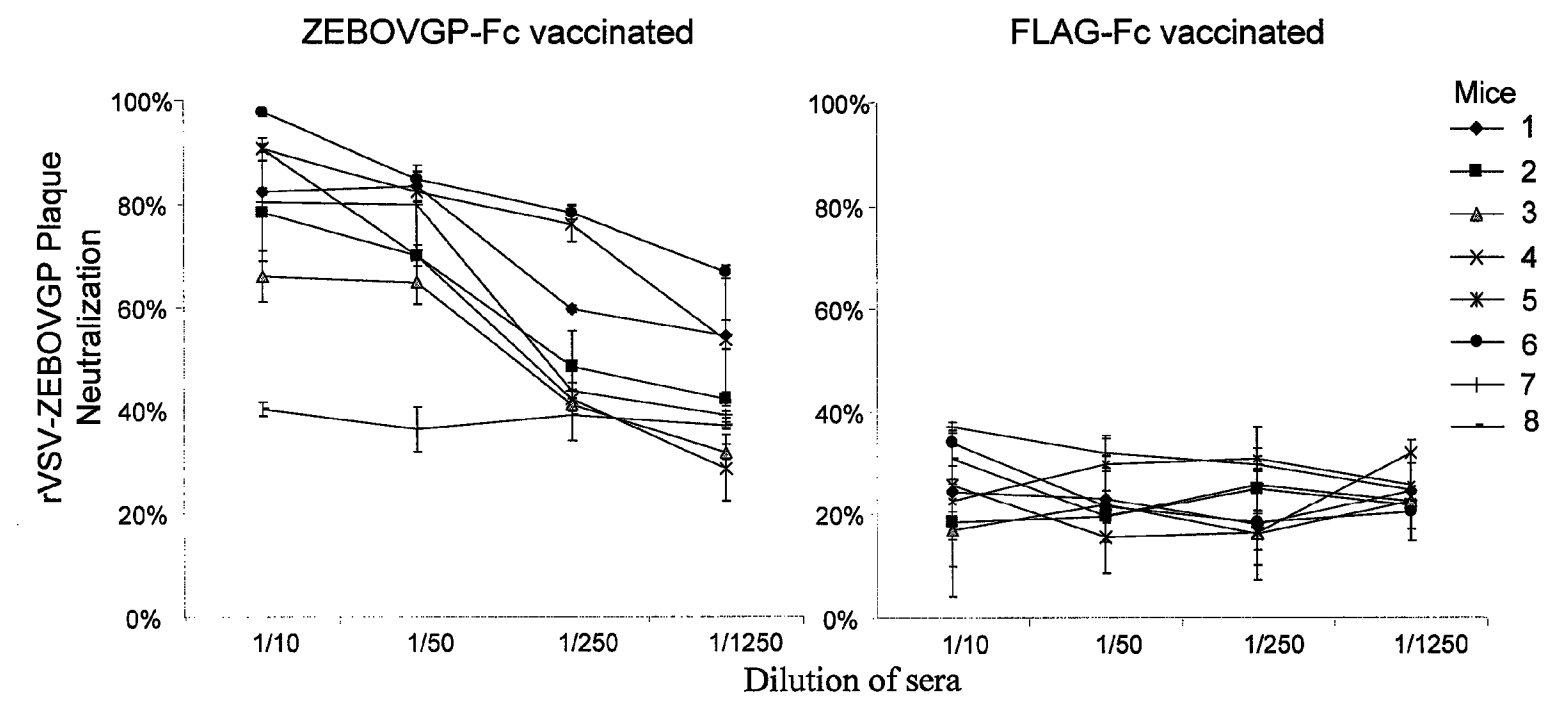

FIG. 4 shows neutralization of rVSV-ZEBOVGP with sera from vaccinated C57BL/6 mice. A plaque reduction assay was performed in Vero E6 cells using 100 pfu of rVSV-ZEBOVGP treated with five-fold dilutions of sera from mice vaccinated with ZEBOVGP-Fc or FLAG-Fc. Percent neutralization of each mouse serum was calculated as the reduction in the number of plaques compared to untreated rVSV-ZEBOVGP. The data show the mean percent neutralization in duplicate samples for each mouse sera dilution, and bars represent the standard deviations.

Figure 5:
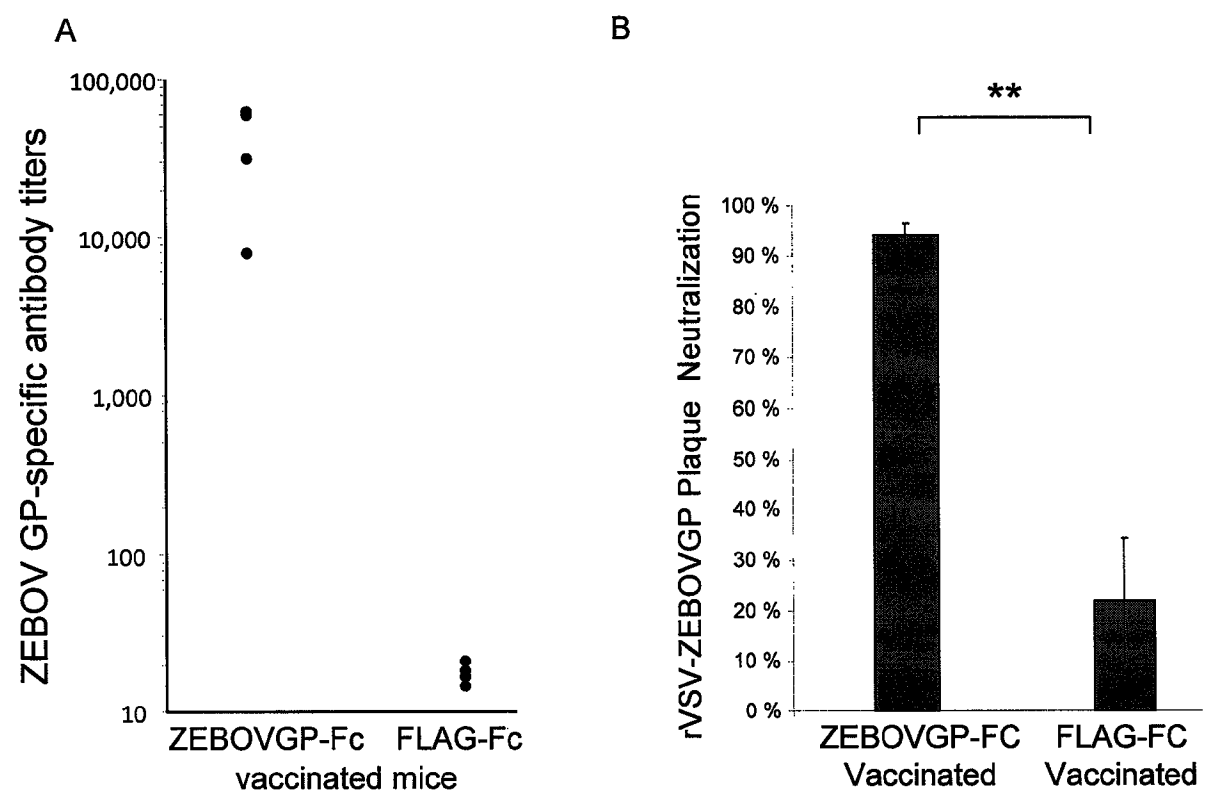

FIG. 5 shows humoral immune response in BALB/c mice vaccinated with ZEBOVGP-Fc. Four BALB/c mice were immunized with ZEBOVGP-Fc or FLAG-Fe. Sera samples were collected 2 weeks after the final vaccination. A) Analysis of anti-ZEBOV GP-specific antibodies by viral particle ELISA on plates coated with rVSV-ZEBOVGP was done as described in FIG. 3A. B) Neutralization of rVSV-ZEBOVGP with sera from BALB/c mice vaccinated with ZEBOVGP-Fc or FLAG-Fc. Mean neutralization with 1/10 dilution sera was determined by a plaque reduction assay using duplicate samples as described in FIG. 4. The data show the mean (n=4) of the percent mean neutralization of each sample, and bars represent the standard deviation. The difference between neutralization of sera from ZEBOVGP-Fc- and FLAG-Fc-vaccinated mice is statistically significant (**, $p<0.01$).

FIG. 6 shows cellular immune response in BALB/c mice vaccinated with ZEBOVGP-Fc. Splenocytes from vaccinated BALB/c mice in FIG. 5 were collected eight days after the final immunization, stimulated with fusion proteins or peptides, and stained at the cell surface with APC-labeled anti-CD8 mAb and intracellularly with PE-labeled anti-IFN-γ mAb. The percent of IFN-γ-producing $CD8^+$ T-cells was determined by flow cytometry gating on $CD8^+$ splenocytes. A) Dot plot analysis of $CD8^+$ splenocytes from a representative mouse vaccinated with ZEBOVGP-Fc or FLAG-Fc and stimulated with ZEBOVGP-Fc or FLAG-Fc. Double-positive splenocytes expressing CD8 and IFN-γ are shown within a rectangular box and numbers represent the percentage of IFN-γ-positive $CD8^+$ cells within the box. B-E) Bar graph representation of the percentage of IFN-γ-positive $CD8^+$ cells in splenocytes from mice vaccinated with ZEBOVGP-Fc (B,D) or FLAG-Fc (C,E) and stimulated with Fc fusion proteins (B,C) or synheic peptides (D,E). Splenocytes were stimulated with Fc fusion proteins ZEBOVGP-Fc or FLAG-Fc, or ZEBOV GP-specific or control synthetic peptides. The data represent the mean percentage of total CD8+ cells that express IFN-γ (n=4 mice), and the bars represent the standard deviations. The difference between the percentage of IFN-γ-positive $CD8^+$ splenocytes in ZEBOVGP-Fc-vaccinated mice stimulated with ZEBOVGP-Fc and FLAG-Fc is statistically significant (*, $p=0.01$).

Figure 7:
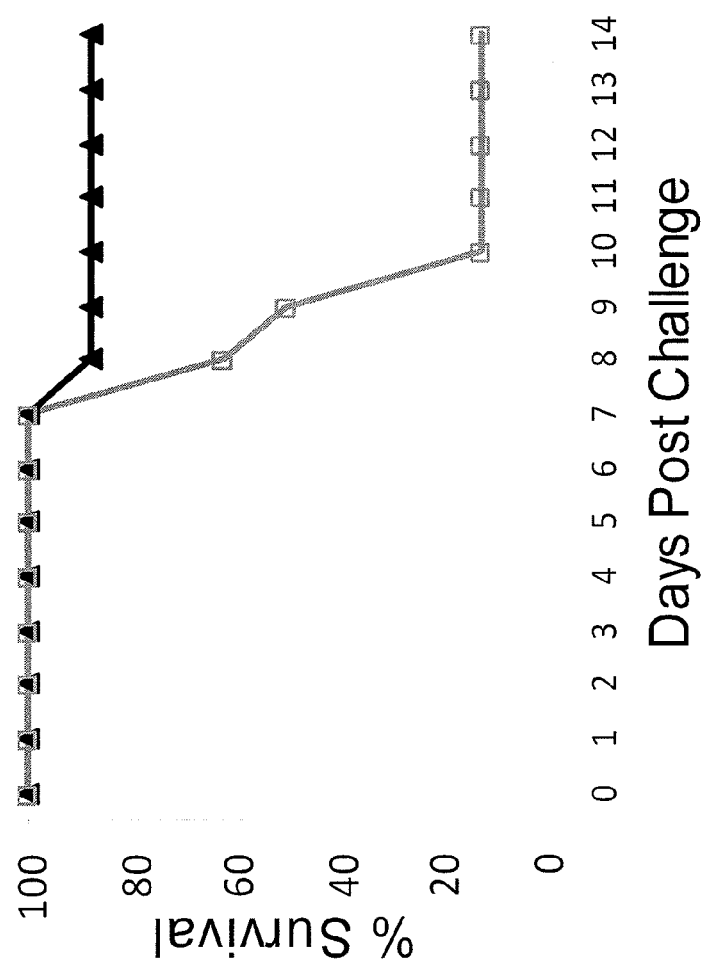

FIG. 7 shows that ZEBOVGP-Fc protected mice against a ZEBOV lethal challenge. Mice were vaccinated with ZEBOVGP-Fc (filled triangle) or FLAG-Fc (open squares) and challenged with 1,000 pfu of mouse adapted ZEBOV two weeks after the last vaccination. Results are plotted as percent survival for each vaccination group (n=8 mice per group).

Figure 8:
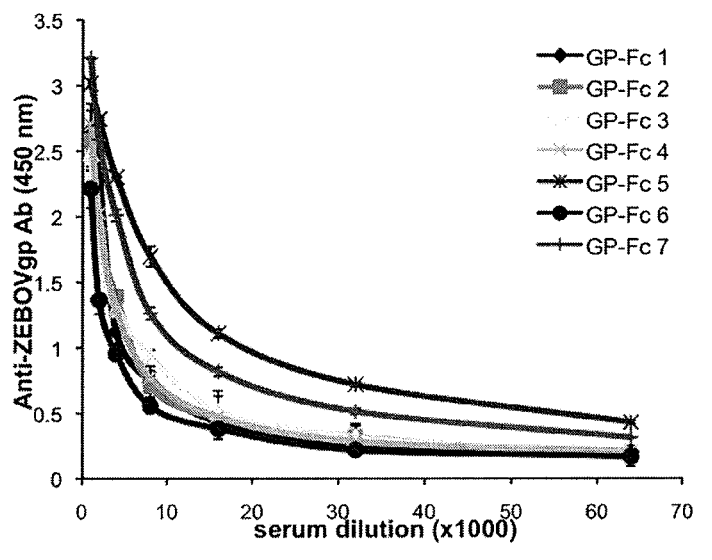

FIG. 8 shows the results of experiments of virus particle ELISA of sera from guinea pigs vaccinated with ZEBOVGP-Fc fusion protein. Seven guinea pigs (GP-Fc 1 to GP-Fc7) were vaccinated with ZEBOVGP-Fc in QS-21 adjuvant. Animals were bled after 2 boosts and sera was analyzed by virus particle ELISA for anti-ZEBOVGP antibodies. All animals develop high titers of anti-ZEBOVGP antibodies.

Figure 9:
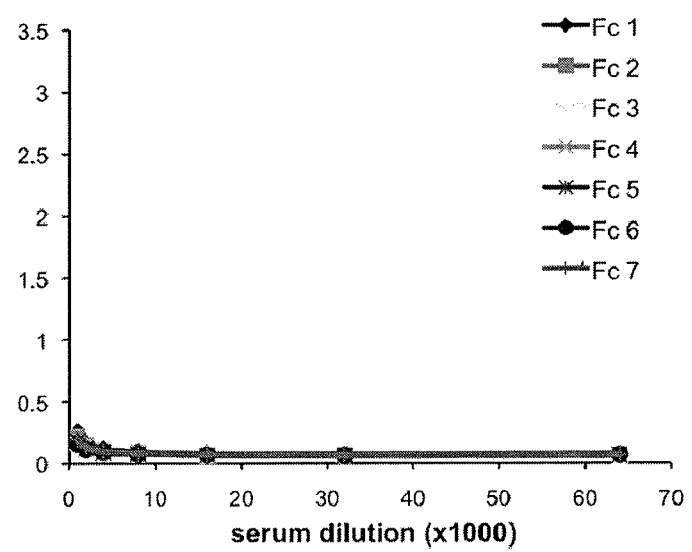

FIG. 9 shows the results of experiments of virus particle ELISA of sera from guinea pigs vaccinated with control Fc fragment. Seven guinea pigs (Fc 1 to Fc7) were vaccinated with Fc fragment alone in QS-21 adjuvant. Animals were bled after 2 boosts and sera was analyzed by virus particle ELISA for anti-ZEBOVGP antibodies. None of the animals develop anti-ZEBOVGP antibodies.

Figure 10:
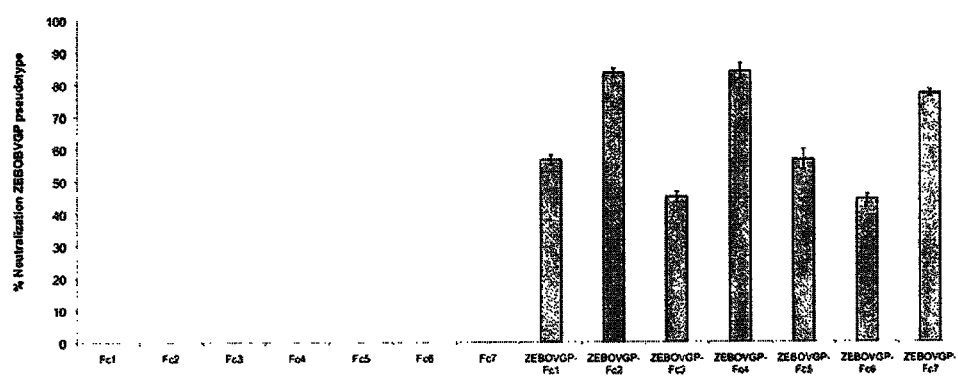

FIG. 10 shows neutralization of Zaire Ebola virus pseudotype with sera from ZEBOVGP-Fc vaccinated guinea pigs. Zaire Ebola virus pseudotypes were neutralized with sera from guinea pigs vaccinated with ZEBOVGP-Fc or Fc fragment alone. Percent neutralization was determined in comparison to neutralization with pre-immune sera. All ZEBOVGP-Fc vaccinated animals developed anti-ZEBOV neutralizing antibodies whereas none of the Fc vaccinated animals developed anti-ZEBOV neutralizing antibodies.

Figure 11:
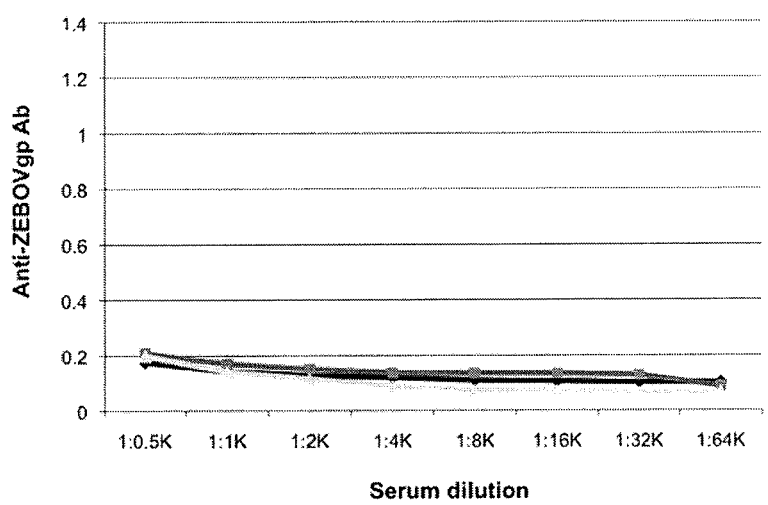

FIG. 11 shows analysis of anti-Ebola virus antibodies in three Rhesus monkeys. Prior to vaccination, sera from three monkeys was tested for anti-Ebola virus GP antibodies by virus particle ELISA. None of the monkeys had anti-Ebola virus antibodies.

Figure 12:
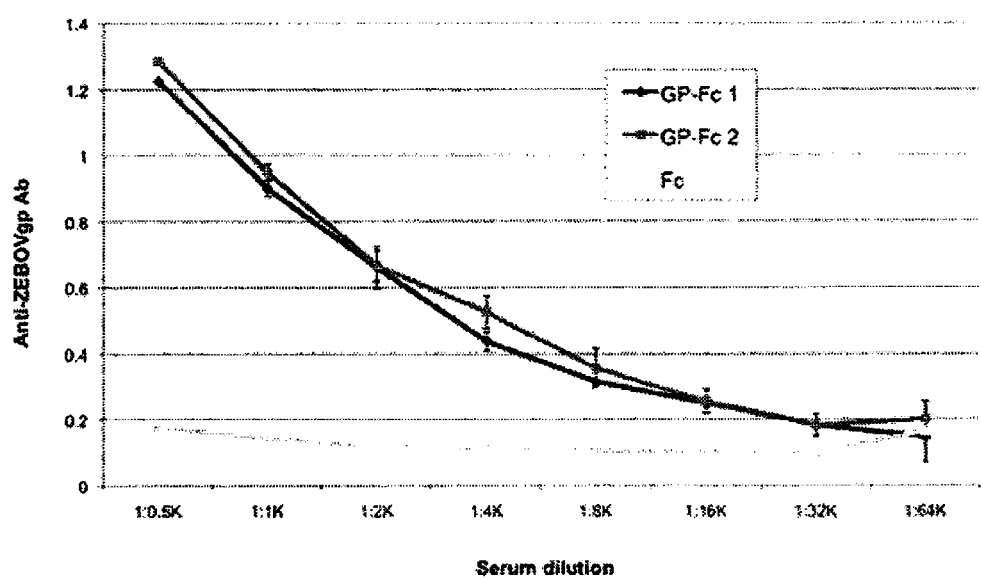

FIG. 12 shows that Rhesus monkeys vaccinated with ZEBOVGP-Fc developed anti-Ebola virus antibodies. Sera from 2 monkeys vaccinated with ZEBOVGP-Fc (GP-Fc1 and GP-Fc2) contained high titers of anti-Ebola virus antibodies as assessed by virus particle ELISA whereas sera from the control monkey vaccinated with Fc fragment alone (Fc) did not develop anti-Ebola virus antibodies.

Figure 13:
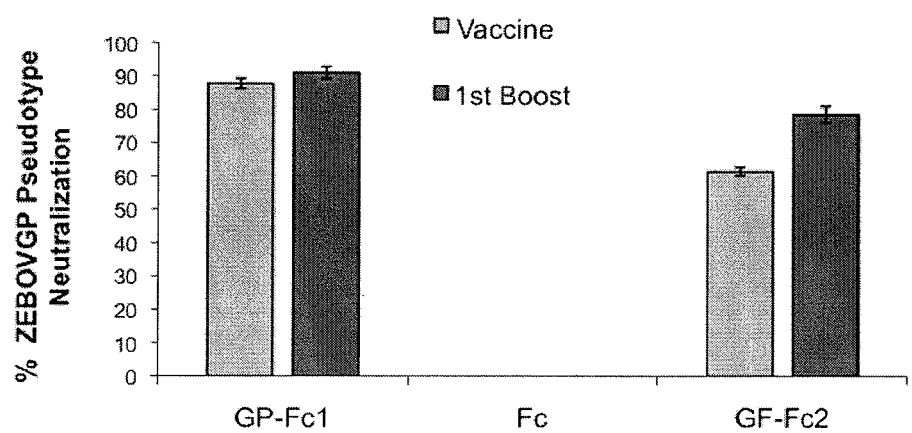

FIG. 13 shows neutralization of Ebola virus pseudotypes with sera from Rhesus monkeys vaccinated with ZEBOVGP-Fc. Sera from Rhesus monkeys GP-Fc1 and -2 that were vaccinated with ZEBOVGP-Fc and control monkey Fc vaccinated with Fc fragment alone was tested for anti-Ebola virus neutralization antibodies by an endpoint dilution assay in 96-well plates containing Vero E6 cell monolayers. Sera was collected 3 weeks after the primary immunization (Vaccine), animals were boosted with the corresponding vaccines and sera was collected 3 weeks after the boost ($1^{st}$ boost). Percent neutralization was determined in comparison to neutralization with pre-immune sera. The ZEBOVGP-Fc inoculated monkeys developed anti-Ebola virus neutralizing antibodies whereas the monkey inoculated with Fc control did not develop neutralizing antibodies.

DETAILED DESCRIPTION

The present invention demonstrates that fusion proteins comprising Filovirus glycoprotein (GP) segment fused to a immunoglobulin polypeptide segment undergo the cleavage and processing observed in native GP. The results presented here clearly indicate that the GP fusion proteins themselves without the need of a viral vector or the assembly into virus-like particles are sufficient for inducing protection against Filovirus infection and are useful as a safe and effective subunit vaccine against Filovirus infection.

As shown in detail below, the extracellular domain of a Filovirus GP (e.g., ZEBOV GP) fused to an immunoglobulin segement (e.g., Fc fragment of human IgG1) expressed in mammalian cells undergoes the complex posttranslational modification including the furin cleavage and homotrimer formation observed in the native GP. Vaccination with the Filovirus GP-IgG fusion protected mice against challenge with a lethal dose of Zaire EBOV. The results presented here demonstrate that the Filovirus GP-IgG fusions, without the need of a viral vector or the assembly into virus-like particles, are sufficient for inducing protection against Filovirus infection and demonstrate that Filovirus GP IgG fusion proteins are useful as cost-effective safe and effective subunit vaccine against Filovirus infection.

Filovirus GP-Immunoglobulin Fusion Proteins

Ebola viruses and Marburg viruses make up the family Filoviridae. There are five species of Ebola viruses, Zaire (type species), Sudan, Reston, Bundibugyo, and Ivory Coast. There is a single species of Marburg virus. The glycoprotein (GP) is the sole structural protein making up the virion surface spikes that mediate virus entry into susceptible host cells through receptor binding. GP is the most studied of the filovirus proteins, not only for its importance in virus entry and pathogenesis but because it is a prime target for vaccine development.

Filovirus particles contain a negative-strand RNA genome of about 19 kb long that encodes seven structural and one nonstructural protein (Volchkov et al., *Adv Virus Res* 2005; 64:359-81). The envelop glycoprotein (GP) is present as spikes on the virion surface and is responsible for receptor binding, viral entry, and immunity (Feldmann et al., *J Gen Virol* 2001 December; 82(Pt 12):2839-48 and Takada et al., *Proc Natl Acad Sci USA* 1997 Dec. 23; 94(26):14764-9). The Filovirus GP is a class 1 integral membrane glycoprotein derived from gene 4 that undergoes a complex processing involving furin cleavage and disulfide-bond formation between the N-terminus and the membrane proximal portion of the GP. The mature transmembrane GP present on the viral envelope and membrane of infected cells is formed by two subunits: the membrane anchored GP2 that is covalently linked via disulphide linkage to the N-terminus of GP 1, which contains a highly o-glycosylated mucin-like domain (Volchkov et al., *Proc Natl Acad Sci USA* 1998 May 12; 95(10):5762-7) and Jeffers et al., *J Virol* 2002 December; 76(24):12463-72). A significant amount of GP1 is shed from the cells after release from the GP2 subunit. In addition, a nonstructural soluble glycoprotein (sGP) that shares the amino-terminal 295 amino acids with GP1, lacks a transmembrane anchor, and forms disulphide-linked homodimers, is produced by EBOV but not MARV infected cells (Feldmann et al., *Curr Top Microbiol Immunol* 1999; 235:1-21).

A number of genes encoding Filovirus GP have been cloned and are described in the literature (see e.g., WO 2006/037038). One of skill can readily clone a desired gene or use genes that have been previously described. Table 1 provides a summary of GenBank Accessions for exemplary GP sequences from various Ebola and Marburg virus subtypes.

TABLE 1

| Virus | Subtype | Genbank Accession No. |
|---|---|---|
| Ebola | Ivory Coast | U28006 |
| | Reston | U23152, NC_004161, AF034645, U23416, AY769362, AF522874, U23417 |
| | Sudan | U28134, U23069, Q66798, AY729654, AY344234, AY316199 |
| | Zaire | AY142960, AF499101, AF272001, AF086833, U23187, NC_002549, AY354458, U28077, U31033, P87666, U81161, AY058898, U77384, AY526105, AY526104, AY526103, |

TABLE 1-continued

| Virus | Subtype | Genbank Accession No. |
|---|---|---|
| | | AY526102, AY526101, AY526100, AY526099, AY526098 |
| | Bundibugyo | ACI28624, FJ217161 |
| Marburg | | Z12132, AF005735, NC_001608, Z29337, X68493, AY358025, AF005733, AF005734, AY430365, AY430366 |

In the fusion proteins of the present invention, the GP protein can be full-length protein or fragment thereof, for example, the GP extracellular domain. The extracellular domain may derived from a variety of sources. For example, it may be derived from a naturally occurring Filovirus glycoprotein, a mutated Filovirus glycoprotein (e.g., a protein comprising a single point mutation, deletion of one or more amino acids, deletion of one or more domains such as mucin domain), or a chimeric Filovirus GP protein comprising domains of different strains, species, or genera of Filoviruses. As noted above, the GP protein of Ebola virus is well characterized and one of skill can easily identify the appropriate domain in the GP protein of a particular isolate. For example, in the exemplified GP described below, a fragment comprising the extracellular domain (residues 1-637 of the polypeptide sequence shown in GenBank accession no. U23187) was used. Using well-known sequence alignment techniques, one of skill could readily identify the corresponding fragment in GPs from other isolates.

The immunoglobulin segment of the fusion proteins of the invention can be derived from any class of antibody: IgA, IgD, IgE, IgG, or IgM. In the typical embodiment, human IgG polypeptides are used. As noted above, IgG molecules are categorized into four subclasses, designated IgG1, IgG2, IgG3, and IgG4. DNA sequences encoding human and non-human immunoglobulin chains are well known in the art.

In the usual embodiment, an immunoglobulin heavy chain constant region is used. As noted above, in the case of IgG molecules, the heavy chain constant region comprises the $C_H1$, $C_H2$, and $C_H3$ domains and the hinge region. In some embodiments, an Fc fragment is used. As noted above, in IgG, IgA and IgD, the Fc region corresponds to $C_H2$, and $C_H3$ domains and the hinge region. In IgM and IgE, the Fc regions contain three heavy chain constant domains ($C_H2$, $C_H3$, and $C_H4$). The hinge can serve as a flexible spacer between the two parts of the fusion protein, allowing each part of the molecule to function independently.

The preparation of fusion proteins comprising immunoglobulin heavy chain constant regions is well known. Many examples of such fusions are described in the literature (see, e.g., U.S. Pat. Nos. 7,754,855; 5,480,981; 5,723,125, 5,808, 029; WO97/23614; WO98/28427 and references cited therein). Fc fusion proteins can include variant Fc molecules (e.g., as described in U.S. Pat. No. 7,732,570).

The Filovirus GP segment and immunoglobulin segment can be linked to each other in a variety of ways known to those of skill in the art. For example, the fusion protein a Filovirus GP segment fused to the immunoglobulin segment, wherein the C-terminus of the Filovirus GP segment is attached to the N-terminus of the immunoglobulin segment.

In some embodiments, the fusion protein can further comprise a peptide linker between the two segments. For example, the C-terminus of the Filovirus GP can be linked to the N-terminus of the immunoglobulin segment by a peptide linker. In general, the peptide linker is immunologically inert and is designed to allow proper processing of the Filovirus GP. The peptide linker may comprise, for example, a protease cleavage site or sequences to facilitate isolation of the fusion, such as epitope tags. Design and use of linker peptides is well known in the art.

Also included in the invention are nucleic acid molecules that encode the fusion proteins of the invention. The nucleic acid molecules of the invention may be in the form of RNA or in the form of DNA obtained by cloning or produced synthetically. The DNA may be double-stranded or single-stranded. By "isolated" nucleic acid molecule(s) is intended a nucleic acid molecule, DNA or RNA, which has been removed from its native environment. For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

Nucleic acid molecules of the present invention include DNA molecules comprising an open reading frame (ORF) encoding a fusion protein of the invention and DNA molecules which comprise a sequence substantially identical to those exemplified here but which, due to the degeneracy of the genetic code, still encode a fusion protein of the invention. Thus, in the typical embodiment, the nucleic acid molecules are expression vectors used to express the fusion proteins of the invention. A nucleic acid molecule encoding the polypeptide can be operably linked to regulatory sequences that control transcriptional expression in an expression vector and then, introduced into a host cell. In addition to transcriptional regulatory sequences, such as promoters and enhancers, expression vectors can include translational regulatory sequences and a marker gene which is suitable for selection of cells that carry the expression vector.

The fusion proteins polypeptides of the present invention can be produced in recombinant host cells following conventional techniques. The fusion proteins of the invention can be expressed in a wide variety of host cells, well known to those of skill in the art. For example, the proteins may be expressed in mammalian cells. Examples of suitable mammalian host cells include African green monkey kidney cells (e.g., Vero; ATCC CRL 1587), human embryonic kidney cells (e.g., 293-HEK; ATCC CRL 1573), baby hamster kidney cells (e.g., BHK-21, BHK-570; ATCC CRL 8544, ATCC CRL 10314), canine kidney cells (e.g., MDCK; ATCC CCL 34), Chinese hamster ovary cells (e.g., CHO-K1; ATCC CCL61; CHO DG44), rat pituitary cells (e.g., GH1; ATCC CCL82), HeLa S3 cells (e.g., ATCC CCL2.2), rat hepatoma cells (e.g., H-4-II-E; ATCC CRL 1548) SV40-transformed monkey kidney cells (e.g., COS-1; ATCC CRL 1650) and murine embryonic cells (e.g., NIH-3T3; ATCC CRL 1658).

For a mammalian host, the transcriptional and translational regulatory signals may be derived from mammalian viral sources, for example, adenovirus, bovine papilloma virus, simian virus, or the like, in which the regulatory signals are associated with a particular gene which has a high level of expression. Suitable transcriptional and translational regulatory sequences also can be obtained from mammalian genes, for example, actin, collagen, myosin, and metallothionein genes.

An expression vector can be introduced into mammalian host cells using a variety of standard techniques including calcium phosphate transfection, liposome-mediated transfection, microprojectile-mediated delivery, electroporation, and the like. The transfected cells can be selected and propagated to provide recombinant host cells that comprise the expression vector stably integrated in the host cell genome. Techniques for introducing vectors into eukaryotic cells and techniques for selecting such stable transformants using dominant selectable markers are well known in the art.

The use of transgenic animals to express heterologous proteins is also well-known. Introduction of a recombinant DNA into the fertilized egg of an animal (e.g., a mammal) may be accomplished using any number of standard techniques in transgenic animal technology. See, e.g., Hogan et al., Manipulating the Mouse Embryo: A Laboratory Manual, Cold Spring Harbor Laboratory Press, Cold Spring Harbor, N.Y., 1986; and U.S. Pat. No. 5,811,634. Once the recombinant DNA is introduced into the egg, the egg is incubated for a short period of time and is then transferred into a pseudopregnant animal of the same species from which the egg was obtained. While the entire animal can be used as an expression system for the fusion proteins of the invention, typically, the fusion protein accumulates in products of the animal, from which it can be harvested without injury to the animal. In preferred embodiments, the fusion protein accumulates in milk, eggs, hair, blood, or urine. If the fusion protein is to be accumulated in the milk of the animal, suitable mammals are ruminants, ungulates, domesticated mammals, and dairy animals. Particularly preferred animals are goats, sheep, camels, cows, pigs, horses, oxen, and llamas. Methods for generating transgenic cows that accumulate a recombinant peptide in their milk are well known: see, Newton (1999, J. Immunol. Methods 231:159-167), Ebert et al. (1991, Biotechnology 9: 835-838), and U.S. Pat. Nos. 6,210,736, 5,849, 992, 5,843,705, 5,827,690, 6,222,094.

The fusion proteins of the invention can also be expressed in other higher eukaryotic cells, such as avian, insect, fungal, yeast, or plant cells. The baculovirus system provides an efficient means to introduce cloned genes into insect cells. Fungal cells, including yeast cells, can also be used to express the genes described herein. Yeast species of particular interest in this regard include *Saccharomyces cerevisiae*, *Pichia pastoris*, and *Pichia methanolica*. Suitable promoters for expression in yeast include promoters from GAL1 (galactose), PGK (phosphoglycerate kinase), ADH (alcohol dehydrogenase), AOX1 (alcohol oxidase), HIS4 (histidinol dehydrogenase), and the like. Expression vectors can also be introduced into whole plants (e.g., tobacco plants), plant protoplasts, intact plant tissues, or isolated plant cells. Methods for introducing expression vectors into plant tissue include the direct infection or co-cultivation of plant tissue with *Agrobacterium tumefaciens*, microprojectile-mediated delivery, DNA injection, electroporation, and the like.

Alternatively, genes encoding the polypeptides of the present invention can be expressed in prokaryotic host cells. Suitable prokaryotic hosts include *E. coli* and *Bacillus subtilus*. Suitable strains of *E. coli* include BL21(DE3), BL21 (DE3)pLysS, BL21(DE3)pLysE, DH1, DH4I, DH5, DH5I, DH5IF', DH5IMCR, DH10B, DH10B/p3, DH11S, C600, HB101, JM101, JM105, JM109, JM 110, K38, RR1, Y1088, Y1089, CSH18, ER1451, and ER1647 (see, for example, Brown (ed.), Molecular Biology Labfax (Academic Press 1991)). Suitable strains of *Bacillus subtilus* include BR151, YB886, MI119, MI120, and B170 (see, for example, Hardy, "*Bacillus* Cloning Methods," in *DNA Cloning: A Practical Approach*, Glover (ed.) (IRL Press 1985)).

Methods for expressing proteins in prokaryotic hosts are well-known to those of skill in the art (see, for example, Williams et al., "Expression of foreign proteins in *E. coli* using plasmid vectors and purification of specific polyclonal antibodies," in *DNA Cloning 2: Expression Systems*, 2nd Edition, Glover et al. (eds.), page 15 (Oxford University Press 1995), Ward et al., "Genetic Manipulation and Expression of Antibodies," in *Monoclonal Antibodies: Principles and Applications*, page 137 (Wiley-Liss, Inc. 1995), and Georgiou, "Expression of Proteins in Bacteria," in *Protein Engineering: Principles and Practice*, Cleland et al. (eds.), page 101 (John Wiley & Sons, Inc. 1996)).

Once expressed, the fusion proteins of the present invention can be purified according to standard procedures of the art, including ammonium sulfate precipitation, fraction column chromatography, gel electrophoresis and the like.

Immunogenic Compositions

Purified or partially purified fusion proteins of the invention may be formulated as a vaccine (also referred to as an "immunogenic composition") according to methods well known in the art. Such compositions may include adjuvants to enhance immune responses. The optimal ratios of each component in the formulation may be determined by techniques well known to those skilled in the art. The immunogenic compositions may be administered to a patient according to standard techniques well-known to those of skill in the art. The patient can be a human, or non-human animal (e.g., cattle, horses, pigs, dogs, and cats).

The preparation and use of immunogenic compositions are well known to those of skill in the art. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

The polynucleotides encoding the fusion proteins of the invention can also be administered to the patient. Typically, an expression cassette suitable for driving expression in human cells is prepared. This approach is described, for instance, in Wolff (1990) Science 247:1465-1468; U.S. Pat. Nos. 5,580,859 and 5,589,466.

The compositions are suitable for single administrations or a series of administrations. When given as a series, inoculations subsequent to the initial administration are given to boost the immune response and are typically referred to as booster inoculations. The compositions of the invention can be used as a boosting composition primed by antigen using any of a variety of different priming compositions, or as the priming composition. Thus, one aspect of the present invention provides a method of inducing and/or boosting an immune response to an antigen in an individual.

The timing of the administration of boosting compositions is well within the skill in the art. Boosting composition are generally administered weeks or months after administration of the priming composition, for example, about 2-3 weeks or 4 weeks, or 8 weeks, or 16 weeks, or weeks, or 24 weeks, or 28 weeks, or 32 weeks.

The compositions of the invention may comprise other Filovirus antigens or the priming or boosting inoculations may comprise other antigens. The other antigens used in combination with the fusion proteins of the invention are not critical to the invention and may be, for example, Filovirus antigens, nucleic acids expressing them, virus like particles (VLPs) or replication deficient or competent viral vectors that comprise the nucleic acids, such as the prior art vaccines discussed above. Such viral vectors include, for example, adenoviral vectors, vaccinia virus vectors, avipox vector such as fowlpox or canarypox, herpes virus vectors, a vesicular stomatitis virus vectors, or alphavirus vectors. One of skill will recognize that the immunogenic compositions of the invention may comprise multiple antigens and vectors.

The antigens in the respective priming and boosting compositions (however many boosting compositions are employed) need not be identical, but should share epitopes. The antigen may correspond to a complete antigen in a target pathogen or cell, or a fragment thereof. Peptide epitopes or artificial strings of epitopes may be employed, more efficiently cutting out unnecessary protein sequence in the antigen and encoding sequence in the vector or vectors. For example, one or more additional epitopes may be included, for instance epitopes which are recognized by T helper cells, especially epitopes recognized in individuals of different HLA types.

As noted above, the immunogenic compositions of the invention may comprise adjuvants. Adjuvants suitable for co-administration in accordance with the present invention should be ones that are potentially safe, well tolerated and effective in people including QS-21, Detox-PC, MPL-SE, MoGM-CSF, TiterMax-G, CRL-1005, GERBU, TERamide, PSC97B, Adjumer, PG-026, GSK-I, GcMAF, B-alethine, MPC-026, Adjuvax, CpG ODN, Betafectin, Alum, and MF59 (see Kim et al., 2000 Vaccine 18:597 and references therein).

Other adjuvants that may be administered include lectins, growth factors, cytokines and lymphokines such as alpha-interferon, gamma interferon, platelet derived growth factor (PDGF), granulocyte-colony stimulating factor (gCSF), granulocyte macrophage colony stimulating factor (gMCSF), tumor necrosis factor (TNF), epidermal growth factor (EGF), IL-1, IL-2, IL-4, IL-6, IL-8, IL-10, and IL-12 or encoding nucleic acids therefore.

As noted above, the compositions of the invention may comprise a pharmaceutically acceptable excipient, carrier, buffer, stabilizer or other materials well known to those skilled in the art. Such materials should be non-toxic and should not interfere with the efficacy of the active ingredient. The precise nature of the carrier or other material may depend on the route of administration, e.g., oral, intravenous, cutaneous or subcutaneous, intramucosal (e.g., gut), intranasal, intramuscular, or intraperitoneal routes. Adimnstration is typically intradermal, e.g., subcutaneous or intramuscular.

Intramuscular administration of the immunogenic compositions may be achieved by using a needle to inject a suspension of the fusion protein or nucleic acid encoding it. An alternative is the use of a needless injection device to administer the composition (using, e.g., Biojector™) or a freeze-dried powder containing the vaccine.

For intravenous, cutaneous or subcutaneous injection, or injection at the site of affliction, the fusion protein will be in the form of a parenterally acceptable aqueous solution which is pyrogen-free and has suitable pH, isotonicity and stability. Those of skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives may be included, as required. A slow-release formulation may also be employed.

Typically, administration will have a prophylactic aim to generate an immune response against a Filovirus antigen before infection or development of symptoms. Diseases and disorders that may be treated or prevented in accordance with the present invention include those in which an immune response may play a protective or therapeutic role. In other embodiments, the Filovirus glycoprotein Fc fusion proteins can be administered for post-exposure prophylactics.

The immunogenic compositions containing the fusion proteins or polynucleotides encoding them are administered to a subject, giving rise to an anti-Filovirus immune response in the subject. An amount of a composition sufficient to in induce a detectable immune response is defined to be an "immunologically effective dose." As shown below, the immunogenic compositions of the invention induce an antibody response, as well as a CD8+ T cell immune response. In a typical embodiment the immune response is a protective immune response.

The actual amount administered, and rate and time-course of administration, will depend on the nature and severity of what is being treated. Prescription of treatment, e.g., decisions on dosage etc., is within the responsibility of general practitioners and other medical doctors, or in a veterinary context a veterinarian, and typically takes account of the disorder to be treated, the condition of the individual patient, the site of delivery, the method of administration and other factors known to practitioners. Examples of the techniques and protocols mentioned above can be found in Remington's Pharmaceutical Sciences, 16th edition, Osol, A. ed., 1980.

Following production of Filovirus glycoprotein Fc fusion proteins and optional formulation of such particles into compositions, the fusion proteins may be administered to an individual, particularly human or other primate. Administration may be to humans, or another mammal, e.g., mouse, rat, hamster, guinea pig, rabbit, sheep, goat, pig, horse, cow, donkey, dog or cat. Delivery to a non-human mammal need not be for a therapeutic purpose, but may be for use in an experimental context, for instance in investigation of mechanisms of immune responses to the fusion protein.

In one exemplary regimen, the fusion protein is administered (e.g., intramuscularly) at a dose of 10 micrograms to 1 milligrams/injection. A boost can be administered up to 4 weeks later. The composition may, if desired, be presented in a kit, pack or dispenser, which may contain one or more unit dosage forms containing the active ingredient. The kit, for example, may comprise metal or plastic foil, such as a blister pack. The kit, pack, or dispenser may be accompanied by instructions for administration.

The compositions of the invention may be administered alone or in combination with other treatments, either simultaneously or sequentially dependent upon the condition to be treated.

Detection of Immune Responses

The fusion proteins of the invention are useful in the detection of Filovirus infection. Methods for detecting humoral or cellular immune responses in biological samples are well known in the art. As used herein, a "biological sample" is any lymphocyte or antibody-containing sample obtained from a patient. For example, the sample can be whole blood, sputum, serum, plasma, saliva cerebrospinal fluid or urine. The proteins of the invention are used in an assay, for example as described below, to determine the presence or absence of antibodies or immune cells (e.g., lymphocytes, CD4+ T-cells, CD8+ T-cells, B-cells, NK cells, mast cells, antigen presenting cells) reactive with Filovirus antigens. The presence of such antibodies or immune cells indicates previous sensitization to Filoviral antigens which may be indicative of Filovirus infection.

There are a variety of assay formats known to those of ordinary skill in the art for using one or more polypeptides to detect antibodies in a sample. For example, the assay may involve the use of a fusion protein immobilized on a solid support to bind to and remove the antibodies from the sample. The assay may also involve the capture of the fusion protein by an antibody or binding protein (e.g., protein A, protein G, protein A/G, avidin, streptavidin, etc.) bound to a solid support. The assay may involve the labeling of the fusion protein with small molecules such as biotin, enzymes, or fluorophores. Alternatively, antibodies from patients could be bound to a solid phase using binding proteins or type specific antibodies (e.g., anti-human IgM or IgG antibodies), followed by treatment with the labeled or unlabeled fusion protein (FiloGP-Fc), and finally detecting the bound fusion protein with a conjugated antibody and/or a binding protein (e.g., avidin-FITC, avidin-peroxidase, etc.). The fusion protein can be isolated or expressed on the surface of a recombinant virus (e.g., Vesicular Stomatitis Virus). The bound antibody may then be detected using a detection reagent that contains a reporter group. Suitable detection reagents include antibodies that bind to the solid phase bound fusion protein or antibody/polypeptide complex or to free polypeptide labeled with a reporter group (e.g., in a semi-competitive assay). Alternatively, a competitive assay may be utilized, in which an antibody that binds to the polypeptide is labeled with a reporter group and allowed to bind to the immobilized antigen after incubation of the antigen with the sample. The extent to which components of the sample inhibit the binding of the labeled antibody to the polypeptide is indicative of the reactivity of the sample with the immobilized polypeptide. In certain embodiments, the assay is an enzyme linked immunosorbent assay (ELISA), chemiluminescent assay, or fluorescence assay.

Methods for detecting cellular immune responses are also well known. In such assays antigen presenting cells, immune cells (e.g., $CD8^+$ T-cells, CD4+ T-cells, B-cells, etc.) and fusion proteins of the invention are incubated under appropriate conditions to induce proliferation or activation of immune effector cells (e.g., $CD8^+$ T-cells, CD4+ T-cells, B-cells, NK and iNKT cells, etc) specific to the Filovirus protein. The antigen-specific responses of induced immune effector cells (e.g., helper T-cells, CTLs, B-cells, NK, NKT, etc.) can be detected by a number of techniques (e.g., by a $^{51}Cr$ release assay, $^3H$-thymidine incorporation, CFSE and other FACS-analysis proliferation assays, cytokine intracellular staining and FACS analysis, ELISPOT, detection of secreted cytokines such as INF-$\gamma$).

In some embodiments the ability of antibodies in a sample to neutralize Filovirus infection can be tested. This can be carried out, for example, using a plaque-reduction test or endpoint dilution assay based on the neutralization of a recombinant virus expressing a Filovirus GP. Also, neutralization can be determined by ELISA, microscopy analysis, or FACS analysis staining infected cells with anti-virus antibodies conjugated with small molecules, enzymes, or fluorophores and/or secondary antibodies or binding proteins (e.g., avidin) conjugated to enzymes or fluorophores. Alternatively, neutralization of recombinant viruses expressing Filovirus GP and containing fluorescent protein genes (e.g., GFP, YFP, etc.) could be determined by the reduction in fluorescent infected cells using fluorescent microscopy analysis or FACS analysis. For example, a recombinant Vesicular Stomatitis Virus (VSV) expressing a Filoviurs GP can be used in such an assay. As shown below, since neutralizing antibodies against Filoviruses are directed towards GP, the only envelope glycoprotein at the cell surface of the virus, neutralization of recombinant VSV expressing such a protein mimics neutralization of Filoviruses. Total antibodies can also be detected by a VSV particle ELISA coating plates with a recombinant Vesicular Stomatitis Virus (VSV) expressing a Filoviurs GP. Methods for carrying out neutralization assays are well known to those of skill in the art. An exemplary assay is described in detail below.

The invention having been described, the following examples are offered by way of illustration and not limitation.

EXAMPLES

The following examples are offered to illustrate, but not to limit the claimed invention.

Example 1

1. Materials and Methods
1.1. Cells Lines

Chinese hamster ovary (CHO) cells deficient in the enzyme dihydrofolate reductase (dhfr⁻) were obtained from the American Type Culture Collection and expanded in growth medium consisting of Iscove's medium containing 10% fetal bovine serum (FBS) (Silberstein et al., *J Virol* 2001 January; 75(2):717-25). Human embryonic kidney HEK293-H cells (Invitrogen) were maintained in Dulbecco's modified Eagle medium (DMEM) supplemented with 10% FBS. Vero E6 cells were grown in Eagle's minimal essential medium (MEM) supplemented with 10% FBS. Baby hamster kidney cells (BHK-21) were maintained in DMEM medium supplemented with 5% FBS. The BSR-T7 cells, which are BHK-21 cells that express bacteriophage T7 RNA-polymerase Buchholz et al., *J Virol* 1999 January; 73(1):251-9), was kindly provided by Dr. K. Conzelmann (Pettenkoffer Institute, Munich, Germany) and maintained in DMEM medium supplemented with 5% FBS and 1 mg/ml geneticin (Invitrogen).

1.2. Mice

C57BL/6 and BALB/c mice were obtained from the National Cancer Institute, Frederick Cancer Research and Development Center (Frederick, Md.). All mice were housed in micro-isolator cages and provided standard rodent feed and water ad libitum. Blood samples were obtained from the lateral tail vein. Research was conducted in compliance with the Animal Welfare Act and other federal statutes and regulations relating to animals and experiments involving animals and adheres to principles stated in the guide for the Care and Use of Laboratory Animals, National Research Council, 1996. The facility where these researches were conducted is fully accredited by the Association for Assessment and Accreditation of Laboratory Animal Care International. The animal protocols were approved by CBER-FDA or USAMRIID Institutional Animal Care and Use Committees (IACUC).

1.3. Cloning Procedures

The cDNA of the Zaire Ebola virus (ZEBOV) glycoprotein (GP), Mayinga strain (GenBank accession no. AF272001), in pVR-1012-ZEBOV-GP was kindly provided by Dr. Gary Nabel, Vaccine Research Center, NIH, Bethesda, Md. Yang et al., *Nat Med* 2000 August; 6(8):886-9). The glycoprotein gene has eight adenosine (A) residues at the RNA editing site needed to produce the full-length ZEBOV GP. The following plasmids were constructed using standard technique of genetic engineering:

1.3.1. pEF1-EBOV-GP

The GP region was excised from pVR-1012-ZEBOV-GP using NcoI and Asp718 (Roche Applied Science) restriction enzymes, filled in with DNA polymerase Klenow (New Engalnd Biolabs) enzyme to create blunt ends and subsequently cloned into the EcoRV site of the mammalian expression plasmid pEF1/Myc-His-B (Invitrogen). The resulting plasmid was termed pEF1-EBOV-GP.

1.3.2. pEF-ZEBOVGP-Fc

To construct a plasmid for the expression of an ZEBOV GP Fc fusion protein, a PCR fragment coding for amino acids 1 to 637 (GenBank accession no. U23187) of the ZEBOV GP ectodomain was amplified from pVR-1012-ZEBOV-GP using synthetic oligonucleotides GP/SalI (5'-GTCGACAGTATGGGCGTTACAGGAATATTGCAGTTA-3'), which contains SalI site before the sequence coding for the signal peptide GP, and GP/Flag/SpeI (5'-ACTAGTACTCACCTCCCTTGTCATCGTCGTCCTTGTAGTCTCCACCGCCGTCCGGAAG GGTTTTATCAACAAA-3'), which contains an SpeI site followed by an artificial splicing donor site, the coding sequence for the FLAG tag peptide DTKDDDDK, and nucleotides 1887 to 1911 of GP. This PCR fragment was cloned into the SalI and SpeI sites of pEF-ICAM5(1-2) Fc replacing the ICAM 1 cDNA fragment and in-frame with the Fc fragment of human IgG1 Silberstein et al., *J Virol* 2001, supra. Silent mutations (GTCGAC to GTAGAC, and CTAGTT to CTCGTT) were introduced into the GP coding sequence to eliminate internal SalI and SpeI restriction sites. The resulting plasmid was termed pEF-ZEBOVGP-Fc.

1.3.3. pEF-FLAG-Fc

To construct a plasmid for the expression of the Fc fragment of human IgG1, we replaced the ICAM 1 sequence in pEF-ICAM5(1-2)Fc with a cDNA fragment coding for the signal peptide of the ZEBOV GP and a FLAG tag. To do so, we amplified a PCR fragment coding for amino acids 1-32 of the ZEBOV GP signal peptide using pVR-1012-ZEBOV-GP as a template and synthetic oligonucleotides GP/SalI (see above) and SP/Flag/SpeI (5'-ACTAGTACTCACCTCCCTTGTCATCGTCGTCCTTGTAGTCTCCACCGCCGGAAAATGTTCTTTGGAAAAGGAT-3'), which codes for a FLAG tag, nucleotides 73 to 96 of the GP cDNA, and an SpeI restriction site. The amplified PCR fragment was digested with SalI and SpeI restriction enzymes and cloned into pEF-ICAM5(1-2)Fc digested with the same enzymes. The resulting plasmid was termed pEF-FLAG-Fc.

1.3.4. pVSV-ZEBOVGP

To construct replication-competent VSV-G deleted recombinant Vesicular Stomatitis Virus (VSV) expressing the ZEBOV GP (rVSV-ZEBOVGP), a PCR fragment coding for GP of ZEBOV (amino acids 1-676) amplified from pVR-1012-ZEBOV-GP using oligonucleotides GP/NheI(+) (5'ACTAGTAGTATGGGCGTTACAGGAATATTGCAGTTA-3'), which is identical to GP/SalI except for the SalI site that was substituted for an NheI restriction, and antisense primer GP/NheI (−) (5'-GCTAGCCTAAAAGACAAATTTGCATATACAGAA-3'), was cut with NheI and cloned into NheI cut pVSVAG. The resulting plasmid was termed pVSV-ZEBOVGP.

1.4 Selection of HEK-293-H stable transfectants expressing ZEBOV GP at the cell surface HEK293-H cells were transfected with pEF1-ZEBOV-GP or vector pEF1 using Fugene 6 reagent (Roche Applied Science) as suggested by the manufacturer, and stable transfectants were selected with 350 μg/mL geneticin and termed HEK293-ZEBOVGP or HEK293 cells. Single cell clones were produced and analyzed by flow cytometry using anti-ZEBOV GP monoclonal antibody (mAb) 13F6-1-2 (Wilson et al., *Science* 2000 Mar. 3; 287(5458):1664-6, Lee et al., *J Mol Biol* 2008 Jan. 4; 375(1):202-16) to select stable transfectants expressing high levels of ZEBOV GP at the cell surface.

1.5 Production and Purification of Fc Fusion Proteins

Fc fusion proteins were produced in CHO cell transfectants. To do so, CHO dhfr⁻ cells were cotransfected with 0.45 μg of pDHIP and 3.5 μg of pEF-ZEBOVGP-Fc or pEF-Fc using the Fugene 6 reagent as described previously Silberstein et al., *J Virol* 2001, supra. Briefly, cell transfectants were grown in Iscove's medium containing 10% FBS supplemented with hypoxanthine and thymidine for 48 h at 37° C., split 1:10, and selected in Iscove's medium containing dialyzed FBS without supplements. After 14 days of selection, single cell clones were obtained by end-point dilution in 96-well plates. The supernatants of 56 single-cell clones were assayed for the expression of fusion proteins by a capture ELISA in 96-well plates coated with goat anti-human Fc antibody and staining with anti-GP mAb and HRP-conjugated goat anti-mouse antibody (Ab). Overexpression of the Fc fusion proteins was achieved by a stepwise increase in the concentration of methotrexate (MTX). Cells reached a maximum level expression of ZEBOVGP-Fc and FLAG-Fc at 0.08 and 0.32 µM MTX, respectively.

Fc fusion proteins were purified as described previously Silberstein et al., J Virol 2001, supra. Briefly, CHO cells expressing recombinant proteins were grown in Iscove's medium containing 10% FBS for 3 days, monolayers were washed twice with Iscove's medium, and grown in serum-free OptiMEM medium (Invitrogen). Supernatants were harvested 2-3 times at 24 h intervals, clarified at 3,000×g, and stored at −20° C. Fc fusion protein in the OptiMEM supernatant was purified by affinity chromatography in protein A-agarose columns. Eluted fractions were analyzed by denaturing sodium dodecyl sulfate-polyacrylamide gel electrophoresis (SDS-PAGE), and the fractions containing the Fc fusion proteins were pooled, concentrated using Amicon ultra column (Millipore), and washed with PBS.

1.6 Western Blot Analysis

Purified proteins were fractionated in denaturing SDS-PAGE, transferred to Immobilon-P polyvinylidene difluoride (PVDF) membranes (Millipore), and stained with a 1:1,000 dilution of mouse anti-ZEBOV GP 13F6-1-2 mAb (USAMRIID), mouse anti-FLAG M2 mAb (Sigma Chemical Co.), or goat anti-human IgG Fc Ab, and a 1:3,000 dilution of phosphatase-labeled goat anti-mouse or rabbit anti-goat Ab. The Western blot was developed with 5-bromo-4-chloro-3-indolylphosphate-nitroblue tetrazolium substrate (Kpl Inc.) as recommended by the manufacturer.

1.7. Rescue of rVSV-ZEBOVGP

To generate recombinant VSV carrying the ZEBOV GP (rVSV-ZEBOVGP), we used the reverse genetics system developed by Dr. John Rose (Yale Univ., New Haven, Conn.), who kindly provided us with plasmid coding for the VSV full-length genome [pVSVFL(+)], VSV-G deleted VSV genome (pVSVΔG), VSV nucleoprotein (pBS-N), VSV phosphoprotein (pBS-P), and VSV-L polymerase (pBS-L) [27]. To do so, BSR-T7 cells grown to 80-90% confluency in 6-well plates were cotransfected with 0.25 µg pBS-N, 0.6 µg pBS-P, 0.13 µg pBS-L, and 1 µg pVSV-ZEBOVGP or positive control pVSVFL(+) using 5 ul Lipofectamine 2000 (Invitrogen) as a facilitator per well (Lawson et al., Proc Natl Acad Sci USA 1995 May 9; 92(10):4477-81; Garbutt et al., J Virol 2004 May; 78(10):5458-65). After 48 h of incubation at 37° C., supernatants were harvested and used to infect 50% confluent BHK-21 cells. After monolayers developed cytopathic effect (CPE), supernatants containing rVSV-ZEBOVGP or VSV were collected, titrated in Vero E6 cells, and stored at −80° C.

1.8. Enterokinase Cleavage of ZEBOVGP-Fc Protein

The Fc fragment of ZEBOVGP-Fc was removed by treatment with 0.4 µg of restriction protease enterokinase (New England Biolabs) per mg of fusion protein, which cleaved the FLAG peptide that was engineered between the GP and Fc fragments. The digestion product was analyzed by FPLC on a Superdex200 column (GE Healthcare) under non-denaturing conditions. The collected fractions were analyzed by denaturing SDS-PAGE and Western blot analysis staining with anti-ZEBOV GP mAb 13F6-1-2 or anti-Fc fragment Ab and appropriate phosphatase-conjugated secondary Ab.

1.9. Vaccination and ZEBOV Challenge

Six-to-eight week old C57BL/6 mice were vaccinated intraperitoneally (i.p.) with 100 µg of ZEBOVGP-Fc (n=8) or with 100 µg of Fc (n=8) in complete Freunds adjuvant. At 21, 45 and 60 days post inoculation, animals were boosted with 25 µg of the corresponding protein in incomplete Freund adjuvant. Serum samples were obtained from each mouse prior to challenge. Mice were challenged 2 weeks after the final vaccination by i.p. injection with 1,000 pfu of mouse-adapted ZEBOV diluted in PBS (Bray et al., J Infect Dis 1998 September; 178(3):651-6; Bradfute et al., J Immunol 2010 Jan. 1; 184(1):327-35). All ZEBOV-infected mice were handled under maximum containment in a biosafety level-4 (BSL4) laboratory at the U.S. Army Medical Research Institute of Infectious Diseases, Frederick, Md.

1.10. Antibody Titer Determination

Anti-ZEBOV specific Ab was analyzed by ELISA as described previously (Hevey et al., Virology 1998 Nov. 10; 251(1):28-37). Sera from vaccinated mice were titrated by endpoint dilution ELISA on 96-well plates coated with sucrose purified inactivated ZEBOV virions and stained with peroxidase-labeled goat anti-mouse IgG Ab. Titers were determined as the highest dilution at which the absorbance of the sample was greater (two times) than non-specific or no-antigen wells (Warfield et al., Vaccine 2004 Sep. 3; 22(25-26):3495-502). Anti-ZEBOV Ab titers were also determined in parallel using 96-well plates coated with rVSV-ZEBOVGP. Plates coated with VSV were used as specificity control. Sera from vaccinated mice were titrated on the plates, stained with peroxidase-labeled goat anti-mouse IgG Ab, and Ab titers were determined as described above.

For FACS analysis, live HEK293-ZEBOVGP cells expressing ZEBOV GP at the surface or control HEK293 cells transfected with empty vector were stained with 1 µl of sera from vaccinated followed by a PE-conjugated anti-mouse Ab (BD Biosciences). Cells were analyzed in a FACSCanto II flow cytometer (BD Biosciences).

1.11. rVSV-ZEBOVGP Plaque Reduction Assay

Anti-ZEBOV neutralizing antibodies were analyzed by a plaque reduction assay. Five-fold dilutions of sera from vaccinated mice were mixed with 100 pfu of rVSV-ZEBOVGP or control VSV. Samples were incubated at 37° C. for 1 h in the presence of 5% guinea pig serum complement and a standard plaque assay was performed in Vero E6 cells overlayed with medium containing 1% bactoagar (DIFCO). The percent of plaque reduction was calculated by comparing the number of pfu in the neutralized sample versus the input virus Wilson et al., and Warfield et al., supra.

1.12. Intracellular Cytokine Staining

Intracellular cytokine staining was performed by incubating splenocytes from vaccinated mice with EBOV GP peptides or ZEBOVGP-Fc as described (Olinger et al., J Virol 2005 November; 79(22):14189-96). Briefly, splenocytes were isolated by passing spleens through a mesh filtration, washed, and cultured in RPMI 1640 medium containing 10% FBS, 2 mM L-glutamine, 1 mM HEPES, and 0.1 mM nonessential amino acids. Splenocytes were stimulated with 1 µg/ml of three EBOV GP specific peptides (LYDRLASTV, VSTGTGPGAGDFAFHK, and EYLFEVDNL) (Olinger et al., supra and Warfield et al., J Immunol 2005 Jul. 15; 175(2): 1184-91) or an unrelated peptide (KINSTALL) as a negative control. Alternatively, splenocytes were stimulated with 10 µg/ml of ZEBOVGP-Fc or FC protein. After stimulation and 1 h of incubation at 37° C. in the presence of interleukin-2, brefeldin A was added and cells were incubated for 5 h before staining with the APC-conjugated anti-mouse CD8 mAb clone RM4-5 (Invitrogen). Cells were then washed, fixed, and permeabilized using the cytofix/cytoperm kit according to the manufacturer's instructions (BD Biosciences). Intracellular IFN-γ was stained with PE-conjugated rat anti-mouse IFN-γ mAb clone XMG1.2 (Invitrogen), and analyzed by flow cytometry in a FACSCanto II instrument.

1.13. Statistical Analysis

Statistical significance between two means was determined by the unpaired Student's t-test and calculated using Graph Pad software, and p-values were included in the text and figures.

Figure 1:
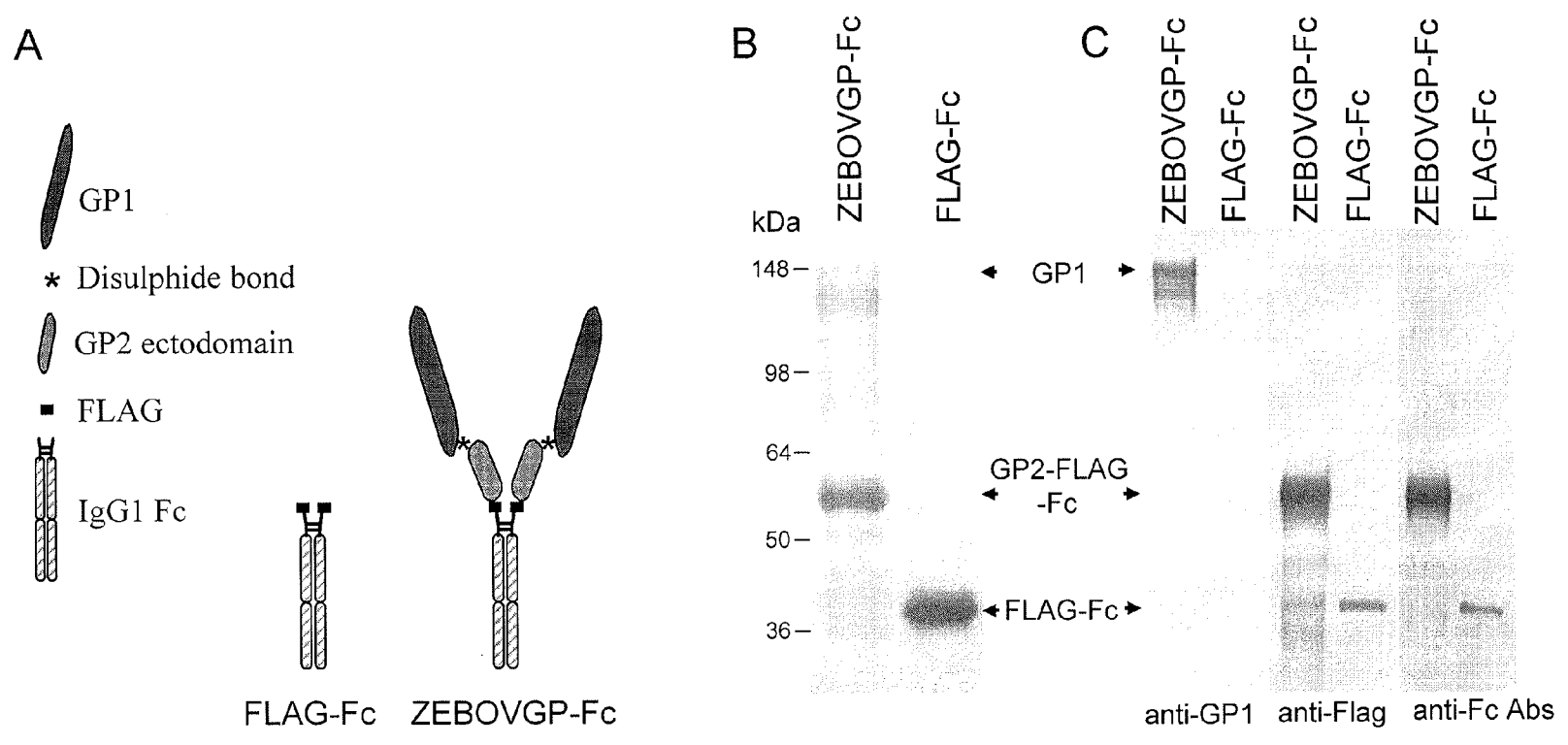

2. Results 2.1. ZEBOVGP-Fc Fusion Protein Undergoes Furin Cleavage and the Complex Processing of Native ZEBOV GP To express large amounts of soluble ZEBOV GP for purification, characterization and immunization purposes, we developed a stable CHO cell line expressing the extracellular domain of ZEBOV GP fused to the human IgG1 Fc fragment. We reasoned that the Fc fragment would increase the yield, simplify purification, and maximize the in vitro and in vivo stability of the recombinant soluble protein (Chamow et al., Trends Biotechnol 1996 February; 14(2):52-60). We also included a FLAG tag epitope between the ZEBOV GP and the Fc fragment to monitor the expression of the chimeric protein with anti-FLAG M2 mAb and also to be able to cleave off the Fc fragment using enterokinase, a restriction protease that cuts at the FLAG tag site. To do so, we cotransfected CHO dhfr-cells with pDHIP, a plasmid coding for the dihydrofolate reductase (DHFR) gene, and pEF-ZEBOVGP-Fc, the construct coding for the ZEBOV GP ectodomain fused to the Fc fragment of IgG1 (FIG. 1A). As a control, we also cotransfected CHO dhfr-cells with pDHIP and pEF-FLAG-Fc, a plasmid coding for the same Fc fragment containing a FLAG tag at the N-terminus. Single cell clones were selected and over expression of the recombinant protein was achieved by increasing the concentration of MTX (Silberstein et al., supra). A CHO cell clone that produced the highest ZEBOVGP-Fc or FLAG-Fc protein yield as measured by ELISA were used for protein production. Protein A purified proteins were analyzed by SDS-PAGE under reducing conditions followed by Coomassie blue staining (FIG. 1B). Two major bands were observed in ZEBOVGP-Fc: a broad band of approximately 130-150 kDa characteristic of highly glycosylated proteins with the expected molecular weight of GP1, and a smaller band of approximately 60 kDa with the expected molecular weight of GP2-Fc. Additional minor bands corresponding to partially glycosylated or degraded proteins were also observed in the ZEBOVGP-Fc lane. The control FLAG-Fc protein migrated as a 36 kDa band. Western blot analysis probing with anti-GP1 mAb 13F6-1-2, anti-FLAG mAb M2, and anti-Fc Ab confirmed the identity of the GP1, GP2-Fc, and FLAG-Fc bands (FIG. 1C). Our data revealed that the ZEBOVGP-Fc fusion protein underwent the complex post-translational modifications of the mature GP including the furin cleavage between GP1 and GP2.

2.2. ZEBOV GP in ZEBOVGP-Fc Assembles into Homotrimers

Figure 2B:
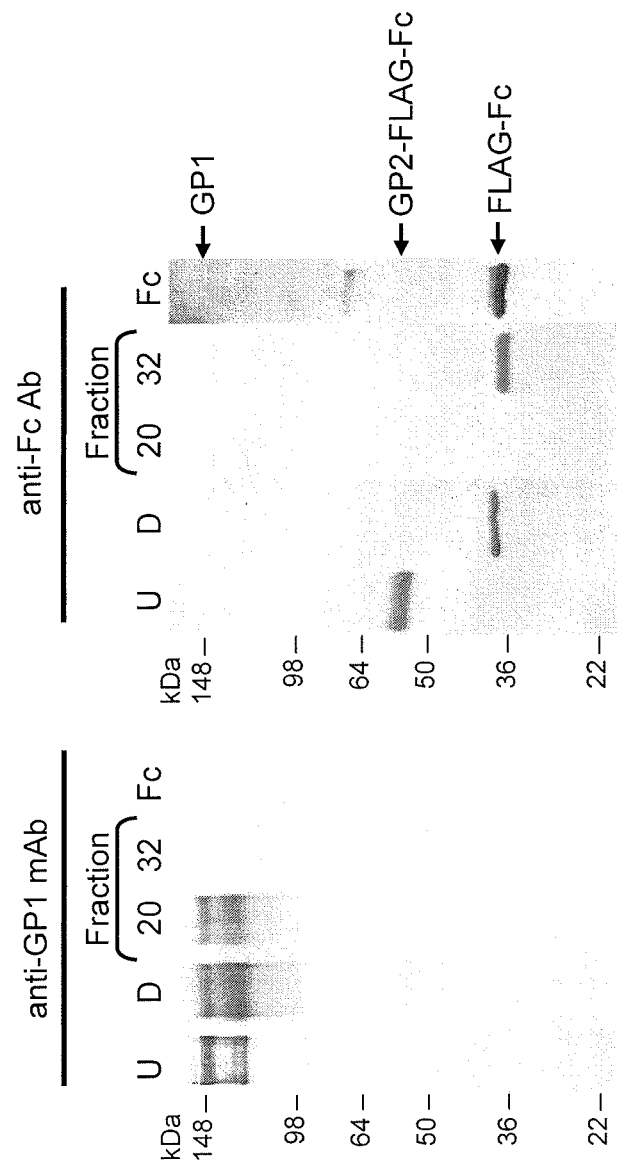

Analysis of purified ZEBOVGP-Fc (50 µg) by size exclusion chromatography through a Superdex 200 10/300 GL column using an AKTA FPLC system (GE) revealed that this fusion protein migrated as a main peak of approximately 1,000 kDa with a broad shoulder consistent with the highly glycosylated nature of GP as observed by SDS-PAGE analysis (FIG. 2A). Since GP forms homotrimers at the virus and cell surface, we hypothesized that the large ZEBOVGP-Fc complexes analysis could be due to GP homotrimer formation, and that 6 copies of ZEBOV-Fc could form 2 homotrimers associated by the disulfide bonds of the Fc fragments, which would have a size of approximately 1,000-1,200 kDa. To test our hypothesis, we digested the ZEBOVGP-Fc (100 µg) with the restriction protease enterokinase (40 ng), which cleaves at the FLAG peptide inserted between GP2 and the Fc fragment. Size exclusion chromatography of this digested product revealed 3 main peaks of approximately 600, 140, 50 kDa (FIG. 2A). We determined that the 140 kDa peak corresponded to a carrier protein present in the enterokinase enzyme preparation. The 600 kDa peak was consistent with the migration of a GP homotrimer formed by GPI (130-150 kDa) and GP2 (25 kDa). The 50 kDa peak had the expected size of an Fc fragment (2 chains of 25 kDa associated by disulfide bonds), and comigrated with the Fc fragment ran under the same conditions (data not shown). Western blot analysis of the 600 and 50 kDa peaks probed with anti-GP1 and anti-Fc antibodies confirmed that the 600 kDa peak corresponded to the GP extracellular domain and the 50 kDa peak corresponded to the Fc fragment (FIG. 2B). These results clearly show that the GP in ZEBOVGP-Fc formed homotrimers resembling the conformation of the natural form of GP expressed on the viral particle and cell surface (Hood et al., J Virol 2010 March; 84(6):2972-82).

2.3. ZEBOVGP-Fc Elicits Anti-ZEBOV Humoral Response in Vaccinated Mice

Figure 3A:
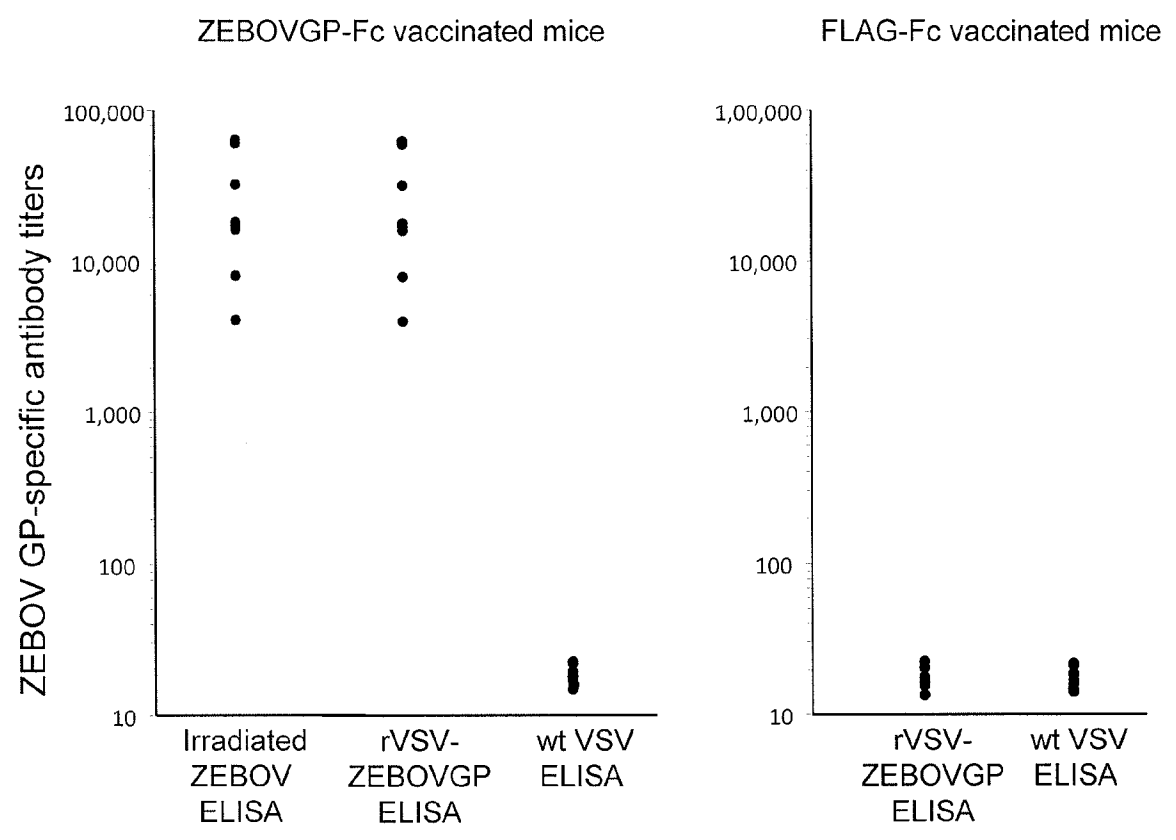

To determine whether ZEBOVGP-Fc was immunogenic, we vaccinated eight C57BL/6 mice with ZEBOVGP-Fc or control FLAG-Fc and tested anti-GP antibodies by ELISA 2 weeks after the final boost. The 8 mice vaccinated with ZEBOVGP-Fc developed anti-ZEBOV GP antibody titers of 1:64,000 to 1:4,000 as measured by an ELISA assay in 96-well plates coated with killed irradiated ZEBOV (FIG. 3A). We also performed a similar ELISA using 96-well plates coated with a purified recombinant VSV containing the ZEBOV GP, rVSV-ZEBOVGP, or wild type VSV as specificity control. The titers determined in the rVSV-ZEBOVGP ELISA were identical to the titers obtained in the killed irradiated ZEBOV ELISA. Sera from control FLAG-Fc vaccinated mice did not react with irradiated ZEBOV or rVSV-ZEBOVGP indicating that the antibodies detected in the vaccinated animals were specific to ZEBOV GP. Moreover, neither sera from ZEBOVGP-Fc nor FLAG-Fc vaccinated animals reacted with wt VSV indicating that the antibodies detected in the ELISA were highly specific to ZEBOV GP.

Figure 3B:
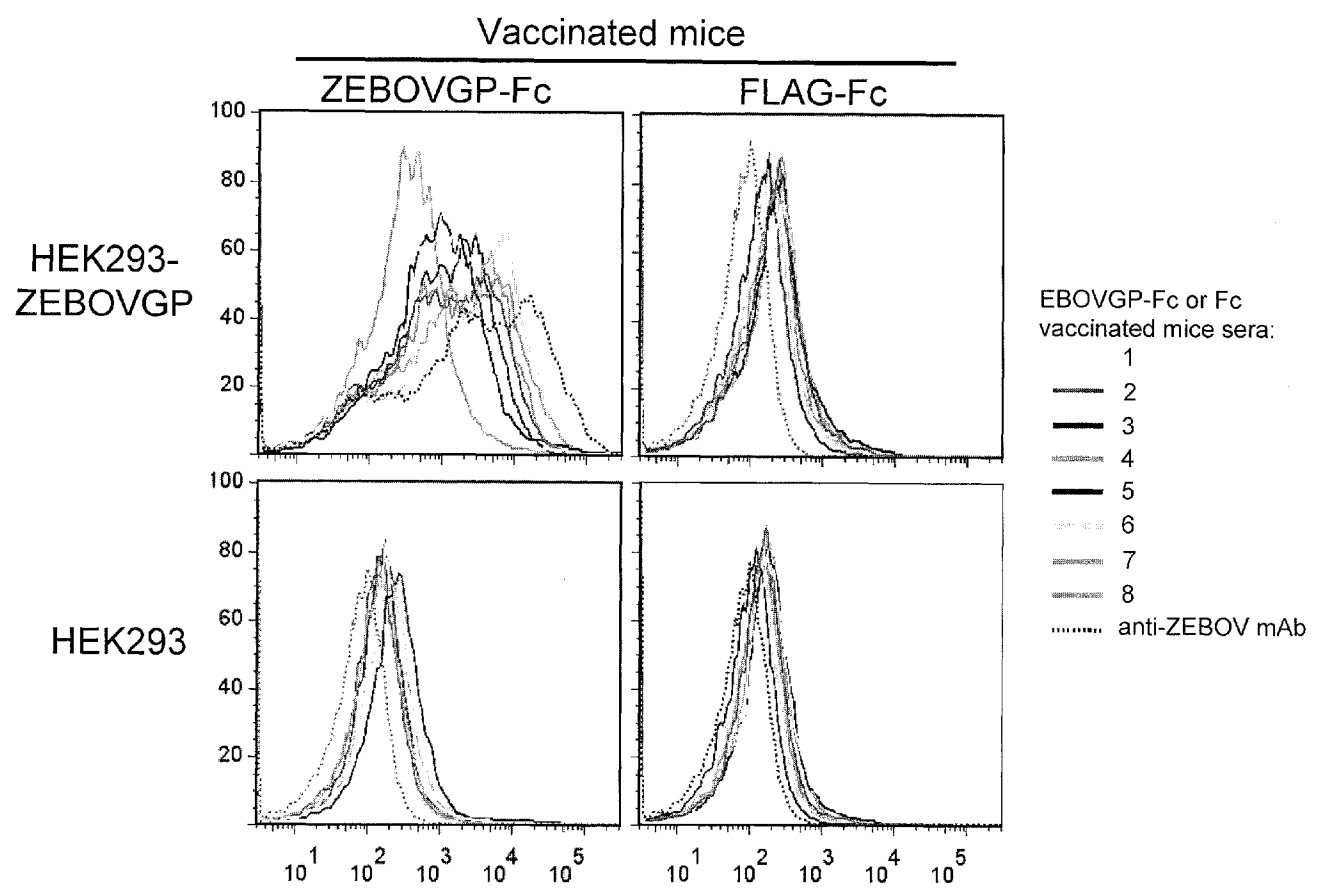

The sera of the vaccinated mice were also tested by FACS analysis on live HEK293 cells expressing EBOV GP protein (HEK293-ZEBOVGP) at the cell surface or vector-transfected cells (HEK293). Sera from ZEBOVGP-Fc immunized mice reacted with the HEK293-ZEBOVGP cells but not with HEK293 cells (FIG. 3B). It should be pointed out that one of the immunized animals reacted poorly with the ZEBOV GP (animal #8). As expected, sera from the FLAG-Fc-vaccinated animals did not react with HEK293-ZEBOVGP or HEK293 cells, and anti-ZEBOV GP mAb 13F6-1-2 reacted only with HEK293-ZEBOVGP cells. These data are consistent with the ELISA data and demonstrated that anti-ZEBOV GP antibodies in the ZEBOVGP-Fc vaccinated animals react with native ZEBOV GP.

2.4. Anti-ZEBOVGP Antibodies Neutralize Recombinant VSV Containing the ZEBOV GP.

Since the vaccinated mice developed anti-ZEBOV GP antibodies, it was of interest to determine whether these antibodies were capable of neutralizing virus. To do so, we performed plaque-reduction test based on the neutralization of rVSV-ZEBOVGP, a replication-competent recombinant VSV-G deleted VSV containing the ZEBOV GP that infect cells via the ZEBOV GP (Lawson et al., and Garbutt et al., supra). Since neutralizing antibodies against ZEBOV are directed towards GP, the only envelope glycoprotein at the cell surface of the virus, neutralization of rVSV-ZEBOVGP mimics neutralization of ZEBOV. Interestingly, all but one mouse (number 8) vaccinated with ZEBOVGP-Fc developed neutralizing antibodies (FIG. 4), and neutralization was antibody-dilution dependent. Mouse number 8 serum also showed low ELISA titers (FIG. 3A) and bound poorly to HEK293-ZEBOVGP cells as assessed by FACS analysis (FIG. 3B). Treatment with sera of mice vaccinated with FLAG-Fc did not neutralize rVSV-ZEBOVGP and resulted in background titer reductions of 40% or lower that were independent of the antibody dilution. These data show that all the mice vaccinated with ZEBOVGP-Fc except number 8 developed neutralizing antibodies against ZEBOV.

2.5. ZEBOVGP-Fc Induces a $CD8^+$ T-Cell Response in Vaccinated Mice

Since protection against Filovirus infection is mediated by humoral and cellular immunity, we analyzed T-cell immunity in mice vaccinated with ZEBOVGP-Fc.

Figure 6A:
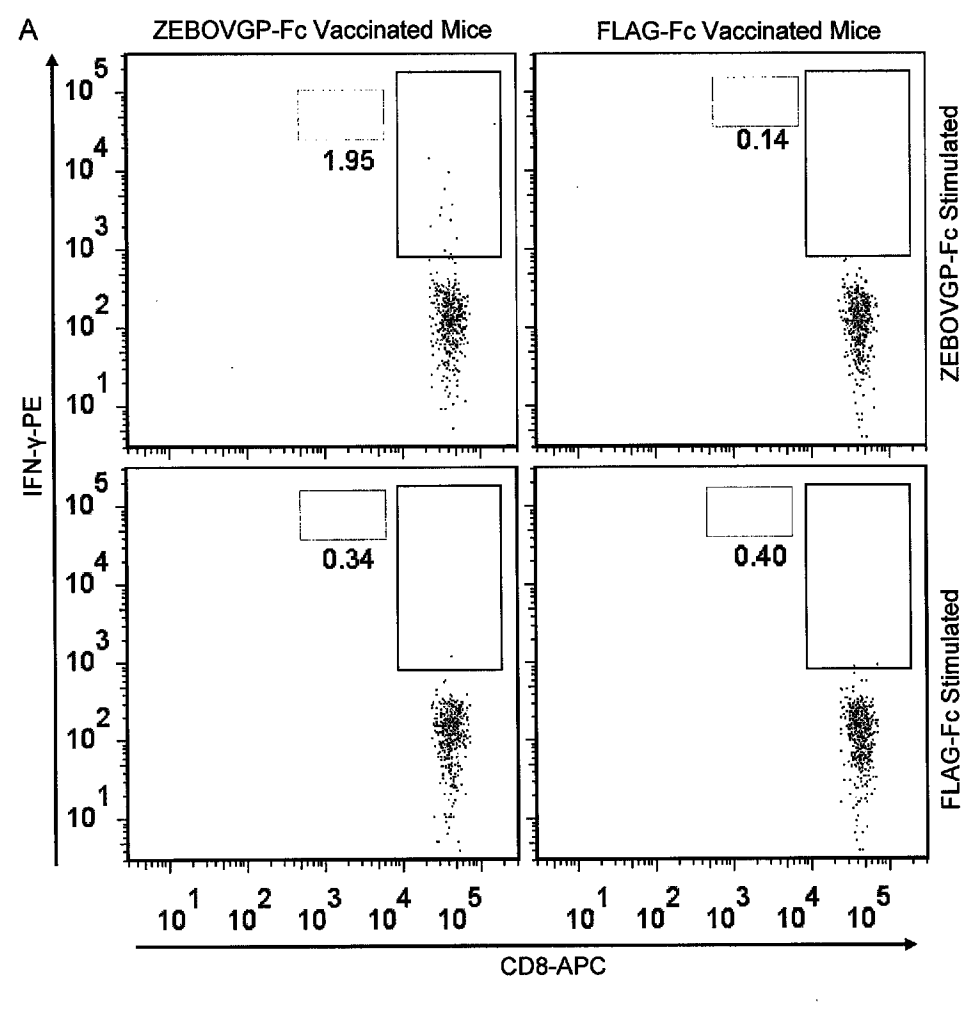
Figures 6B, 6C, 6D, 6E:
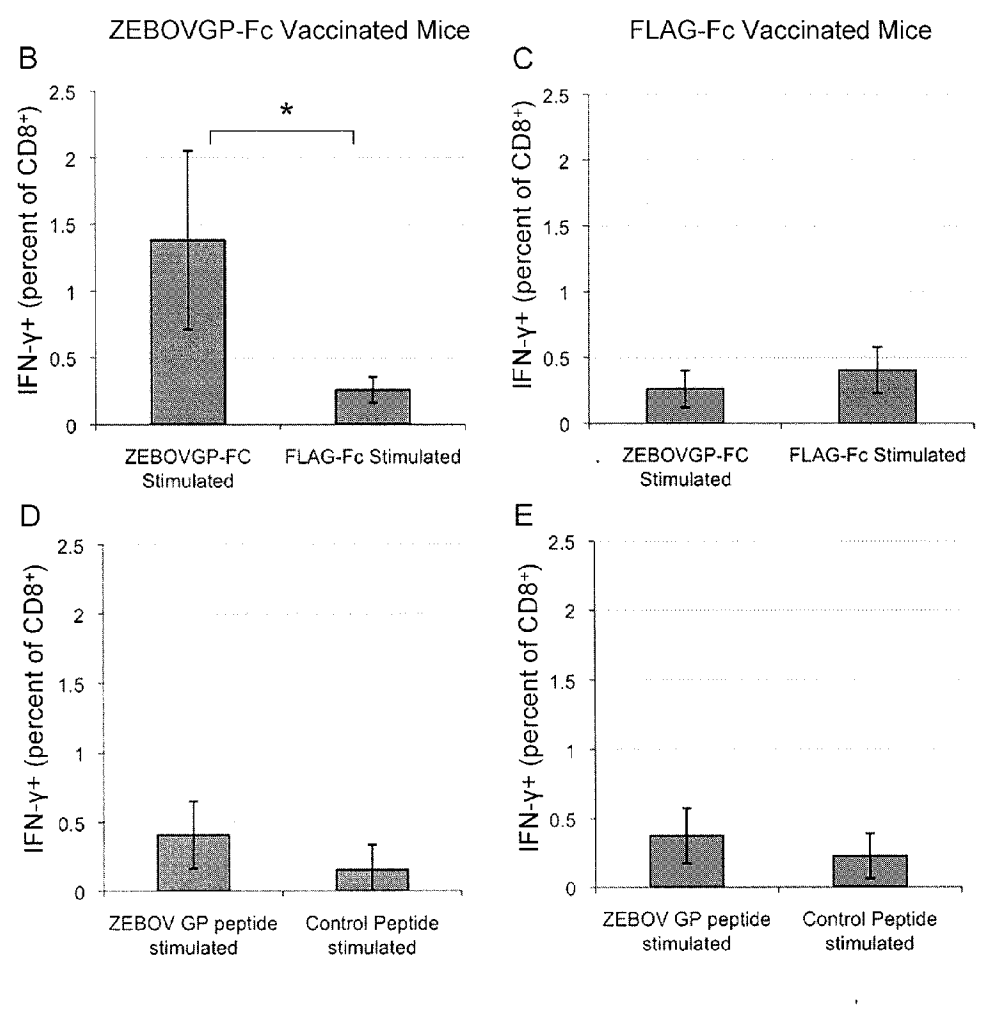

We used BALB/c mice to determine whether ZEBOVGP-Fc could also induced immunity in a different mouse strain. Groups of four BALB/c mice were vaccinated with ZEBOVGP-Fc or FLAG-Fc with the same protocol used for the C57BL/6 mice. The ZEBOVGP-Fc-vaccinated BALB/c mice also developed high titers of anti-ZEBOV GP Ab as assessed by the rVSV-ZEBOVGP viral particle ELISA (FIG. 5A) and neutralizing Ab as determined by the rVSV-ZEBOVGP plaque reduction assay (FIG. 5B). Eight days after the final immunization, mice were euthanized, spleens were harvested, and splenocytes were isolated and stimulated with ZEBOVGP-Fc or ZEBOV GP peptides. A significant increase in IFN-γ-positive $CD8^+$ cells was observed in splenocytes of ZEBOVGP-Fc-vaccinated mice stimulated with ZEBOVGP-Fc compared to FLAG-Fc (FIG. 6A-C). No increase in IFN-γ-positive $CD8^+$ cells was observed in splenocytes of FLAG-Fc-vaccinated mice stimulated with ZEBOVGP-Fc or FLAG-Fc. These data indicated that ZEBOVGP-Fc induced a significant increase in the level of anti-ZEBOV GP IFN-γ-positive $CD8^+$ cells. It should be pointed out that the Fc fragment was a weak inducer of IFN-γ-positive $CD8^+$ cells and resulted in a background level activation of T-cells from both ZEBOVGP-Fc and FLAG-Fc vaccinated mice. Unexpectedly, the ZEBOV GP specific peptides did not activate IFN-γ-positive $CD8^+$ cells in ZEBOVGP-Fc-vaccinated mice (FIG. 6D) compared to FLAG-Fc-vaccinated mice (FIG. 6E).

2.6. ZEBOVGP-Fc Protect Mice Against ZEBOV Challenge

Our results showed that ZEBOVGP-Fc elicited humoral and cellular immune responses in vaccinated mice. Therefore, we tested whether vaccination with ZEBOVGP-Fc could protect mice against a lethal ZEBOV challenge. C57BL/6 mice were vaccinated with ZEBOVGP-Fc or FLAG-Fc and challenged with 1,000 pfu of mouse-adapted ZEBOV seven weeks after the first vaccination (FIG. 7). Seven out of eight mice vaccinated with ZEBOVGP-Fc survived the ZEBOV challenge whereas seven out of the eight mice that received the FLAG-Fc vaccine died within 10 days after challenge. These data showed that EBOVGP-Fc elicited a protective immune response in mice against challenge with ZEBOV.

3. Discussion

The results presented here show that the GP ectodomain in the ZEBOVGP-Fc fusion protein underwent the complex posttranslational modification, including the furin cleavage and disulfide bond formation between the GP1 and GP2 subunits, of the membrane-bound full-length GP. Moreover, FPLC analysis of enterokinase-digested ZEBOVGP-Fc showed that the ZEBOVGP fragment of the Fc fusion protein formed trimers that resemble the natural GP expressed at the viral membrane and cell surface. Vaccination with ZEBOVGP-Fc elicited a humoral immune response that recognized membrane bound GP at the cell and viral particle surface. Interestingly, the anti-GP antibodies reacted similarly with inactivated ZEBOV and rVSV-ZEBOVGP, a replication-competent recombinant VSV particle carrying the ZEBOV GP at the viral surface that induces a protective response in non-human primates (NHP) (Feldmann et al., *PLoS Pathog* 2007 January; 3(1):e2; Jones et al., *Nat Med* 2005 July; 11(7):786-90). The anti-ZEBOVGP-Fc antibodies neutralized rVSV-ZEBOVGP indicating that this fusion protein also elicits protective neutralizing antibodies in NHP. These data show that rVSV-ZEBOVGP is a practical tool to evaluate total and neutralizing antibodies under BSL-2 conditions and indicate that recombinant VSV carrying the Filovirus GP can be used to assess vaccine potency, evaluate consistency in vaccine production, and as a surrogate marker of vaccine efficacy in clinical trials.

Cellular immunity characterized by the production of TNF-α and INF-γ plays a role in the protection against Filovirus infection (Hensley et al., *PLoS Pathog* 2010 May; 6(5): e1000904 and references therein). ZEBOVGP-Fc induced a T-cell response in mice as evidenced by the activation of IFN-γ-positive $CD8^+$ cells in splenocytes stimulated with ZEBOVGP-Fc. Interestingly, stimulation with FLAG-Fc elicited a background level response indicating that the Fc fragment contributed minimally to the cellular response against the fusion protein. In NHP and humans, the human IgG1 Fc fragment present in ZEBOVGP-Fc is likely to be recognized as a self-antigen and may enhance the immunogenicity of the ZEBOVGP-Fc fusion protein by interacting with Fcγ receptors on antigen presenting cells (Zhang et al., *Vaccine* 2009 Feb. 5; 27(6):857-63; Guyre et al., *Cancer Immunol Immunother* 1997 November-December; 45(3-4): 146-8; Chen et al., *Retrovirology* 2007; 4:33). It is not clear why the GP synthetic peptides were ineffective in activating GP-specific T-cells in ZEBOVGP-Fc vaccinated mice. In two studies, these peptides were shown to activate ZEBOV GP-specific T cells in mice under similar conditions used in our assay (Olinger et al., and Warfield et al., supra). However, one of the peptides (LYDRLASTV) failed to activate IFN-γ-positive $CD8^+$ cells in BALB/c mice vaccinated with replication-deficient EbolaΔVP30 virus (Halfmann et al., *J Virol* 2009 April; 83(8):3810). Further research will be required to determine whether ZEBOVGP-Fc vaccination elicited a cellular response against a different set of T-cell epitopes. Taken together, these results clearly show that ZEBOVGP-Fc induced both cellular and humoral immunity against the ZEBOV GP ectodomain.

One mouse vaccinated with ZEBOVGP-Fc did not survive the lethal challenge with ZEBOV. Unfortunately, we did not use individual identifiers at challenge and cannot unequivocally correlate the serology and the survival data. However, it is likely that the ZEBOVGP-Fc vaccinated animal that did not survive the challenge was the only mouse in the group that developed low levels of anti-ZEBOV GP antibodies that failed to neutralize rVSV-ZEBOVGP. Studies are being planned to determine whether the level of neutralizing antibodies against the replication-competent recombinant rVSV-ZEBOVGP correlates with protection against lethal challenge with ZEBOV.

These data indicate that ZEBOVGP-Fc can be used as a subunit Filovirus vaccine for human use. Previous attempts to develop Filovirus subunit vaccines based on soluble forms of Filovirus GP expressed in insect cells provided limited protection against lethal challenge in the guinea pig model (Mellquist-Riemenschneider et al., *Virus Res* 2003 April; 92(2):187-9; Hevey et al., *Virology* 1997 Dec. 8; 239(1):206-16). It is possible that glycosylation in insect cells may have affected epitope structure, homotrimer formation, and stability of the soluble GP protein, factors that could account for the poor performance of the soluble GP vaccine. The ZEBOVGP-Fc used in this study was produced in mammalian cells and most likely resembles the native GP better than the soluble GP expressed in insect cells. In addition, the Fc tag in the ZEBOVGP-Fc conferred several advantages to our vaccine strategy including the ease of purification through protein A columns using mild conditions, an increased protein stability conferred by the Fc fragment, and the adjuvant effect due to the interactions with Fcγ receptors on antigen presenting cells (Zhang et al., Guyre et al.; Chen et al., supra).

These results demonstrate that vaccination with the ZEBOVGP-Fc fusion protein elicited a high level of protection against challenge with ZEBOV and suggested that a subunit vaccine based on Filovirus GP-Fc fusion proteins could be developed to protect against viral infection. This Filovirus GP-Fc can be used as a stand-alone vaccine or in combination with other strategies such as DNA vaccines, virus-like particles, and viral vector vaccines that are currently under development. A subunit vaccine based on Filovirus GP-Fc fusion proteins is simple to produce, easy to purify, and cost-effective and will result in limited adverse events.

EXAMPLE 2

The immunogenicity of FiloGP-Fc was tested in guinea pigs and Rhesus monkeys with a construct containing the complete extracellular domain of the Zaire Ebola virus glycoprotein (ZEBOVGP) fused to the Fc fragment of human IgG1 (ZEBOVGP-Fc). Animals developed a strong anti-ZEBOVGP antibody response and sera neutralized Zaire Ebola virus pseudotypes. The methodology for the protein production, purification, determination of anti-ZEBOVGP antibodies by ELISA, and viral neutralization assays are as described in Example 1. The data presented here show that the FiloGP-Fc proteins are highly immunogenic in guinea pigs and Rhesus monkeys and elicit neutralizing antibodies that are found in the sera of convalescent patients that survived Filovirus infection.

Immunogenicity in Guinea Pigs.

Strain 13 guinea pigs were vaccinated with 0.1 mg of purified ZEBOVGP-Fc or Fc fragment in QS-21 adjuvant. Animals were boosted 2 times with the same dose of the corresponding vaccine at 3 weeks intervals. 2 weeks after the last boost, guinea pigs were bled and the collected sera were used for antibody analysis. Sera from all ZEBOVGP-Fc vaccinated animal contained high antibody titers against ZEBOVGP as assessed by virus particle ELISA (FIG. 8), which ranged from 1/32,000 to 1/128,000. Control guinea pigs vaccinated with the Fc fragment alone (FIG. 9) and pre-vaccination sera from all animals did not contain anti-ZEBOVGP antibodies indicating that the anti-ZEBOVGP antibody response was specific to the viral glycoprotein.

To analyze whether the anti-Ebola virus antibodies elicited by the ZEBOVGP-Fc vaccine could neutralize Ebola virus, sera from vaccinated animals (1:25 dilution) were incubated with ZEBOVGP pseudotype, and neutralization titers were assessed by an endpoint dilution neutralization assay in 96-well plates containing monolayers of Vero E6 cells. After 48 h incubation, wells were examined under the microscope for cytopathic effect due to virus infection. Percent neutralization was calculated compared to pre-immune sera treated virus (FIG. 10). This neutralization assay clearly showed that vaccination with ZEBOVGP-Fc elicited anti-Ebola virus neutralizing antibodies whereas the Fc fragment alone did elicit neutralizing antibodies.

Immunogenicity in Rhesus Monkeys.

Since the results in mice and guinea pigs clearly showed that ZEBOVGP-Fc was highly immunogenic and induced neutralizing anti-Ebola virus antibodies, the recombinant protein was tested to determine whether it could also elicit a strong immune response in Rhesus monkeys (Maccacamulata). To do so, we first determined whether the sera from Rhesus monkeys contained anti-Ebola virus antibodies. Virus particle ELISA revealed that sera from the three monkeys used in our studies did no contain anti-Ebola virus antibodies (FIG. 11).

We then vaccinated two monkeys with 0.4 mg of purified ZEBOVGP-Fc and one monkey control with 0.4 mg of Fc fragment alone using poly(IC) as adjuvant. Three weeks after the primary immunization, the monkeys were bled and then boosted once with the same dose of the corresponding vaccine. Three weeks after the boost, monkeys were bled and sera samples were used for antibody analysis. Sera from the ZEBOVGP-Fc vaccinated animals contained high antibody titers against ZEBOVGP of approximately 1/32,000 as assessed by virus particle ELISA (FIG. 12). As expected, the control monkey vaccinated with the Fc fragment alone did not develop anti-ZEBOVGP antibodies indicating that the anti-ZEBOVGP antibody response was specific for the viral glycoprotein.

To determine whether the monkeys inoculated with the ZEBOVGP-Fc vaccine developed anti-Ebola virus neutralizing antibodies, sera from the vaccinated animals (1:50 dilution) were incubated with ZEBOVGP pseudotype and neutralization titers were assessed by an endpoint dilution neutralization assay in 96-well plates containing monolayers of Vero E6 cells. After 48 h incubation, the 96-well plates were examined under the microscope for cytopathic effect due to the virus infection. Percent neutralization was calculated compared to pre-immune sera treated virus (FIG. 13).

CONCLUSIONS

The data presented here clearly show that the ZEBOVGP-Fc vaccine induced high anti-Ebola virus neutralization titers in guinea pigs and monkeys. Moreover, this vaccine elicited anti-Filovirus neutralizing antibodies that can protect against Filovirus infection.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A fusion protein comprising a Filovirus glycoprotein segment comprising an extracellular domain and an immunoglobulin polypeptide segment comprising an immunoglobulin heavy chain constant domain polypeptide, wherein the C-terminus of the Filovirus glycoprotein segment is attached to the N-terminus of the immunoglobulin polypeptide segment.

2. The fusion protein of claim 1, wherein the Filovirus glycoprotein segment is from an Ebola virus.

3. The fusion protein of claim 2, wherein the Ebola virus is Zaire Ebola virus, Mayinga strain.

4. The fusion protein of claim 1, wherein the immunoglobulin is IgG1.

5. The fusion protein of claim 1, further comprising a linker between the Filovirus glycoprotein segment and the immunoglobulin polypeptide segment.

6. The fusion protein of claim 1, which has the sequence as shown in SEQ ID NO: 2.

7. An immunogenic composition comprising the fusion protein of claim 1.

8. The immunogenic composition of claim 7, further comprising an adjuvant.

9. A method of detecting an immune response against Filovirus in a patient, the method comprising contacting a biological sample from the patient with the fusion protein of claim 1 and detecting an immune response.

10. The method of claim 9, wherein the step of detecting an immune response includes the step of detecting binding of antibodies in the biological sample to the fusion protein.

11. The method of claim 10, wherein the step of detecting binding of antibodies is carried by ELISA, a chemiluminescence assay, or a fluorescence assay.

12. The method of claim 9, wherein the step of detecting an immune response includes the step of detecting a cellular immune response.

13. The method of claim 12, wherein the step of detecting a cellular immune response is carried by detecting IFN-γ or TNF-α.

* * * * *